US010849924B2

(12) United States Patent
Goligorsky et al.

(10) Patent No.: US 10,849,924 B2
(45) Date of Patent: Dec. 1, 2020

(54) COMPOSITIONS AND METHODS FOR RESTORING ENDOTHELIAL GLYCOCALYX

(71) Applicant: NEW YORK MEDICAL COLLEGE, Valhalla, NY (US)

(72) Inventors: Michael S. Goligorsky, Valhalla, NY (US); Dong Sun, Chappaqua, NY (US)

(73) Assignee: NEW YORK MEDICAL COLLEGE, Valhalla, NY (US)

( * ) Notice: Subject to any disclaimer, the term of this patent is extended or adjusted under 35 U.S.C. 154(b) by 0 days.

(21) Appl. No.: 16/138,257

(22) Filed: Sep. 21, 2018

(65) Prior Publication Data

US 2019/0091257 A1 Mar. 28, 2019

Related U.S. Application Data

(60) Provisional application No. 62/563,297, filed on Sep. 26, 2017.

(51) Int. Cl.

| | |
|---|---|
| *A61K 31/728* | (2006.01) |
| *A61P 9/10* | (2006.01) |
| *A61P 9/14* | (2006.01) |
| *A61K 47/69* | (2017.01) |
| *C07K 16/28* | (2006.01) |
| *A61K 47/68* | (2017.01) |
| *A61K 9/127* | (2006.01) |
| *A61K 9/00* | (2006.01) |
| *A61K 9/107* | (2006.01) |

(52) U.S. Cl.
CPC .......... *A61K 31/728* (2013.01); *A61K 9/0019* (2013.01); *A61K 9/1075* (2013.01); *A61K 9/127* (2013.01); *A61K 9/1271* (2013.01); *A61K 47/6849* (2017.08); *A61K 47/6875* (2017.08); *A61K 47/6903* (2017.08); *A61K 47/6907* (2017.08); *A61K 47/6911* (2017.08); *A61K 47/6925* (2017.08); *A61K 47/6929* (2017.08); *A61P 9/10* (2018.01); *A61P 9/14* (2018.01); *C07K 16/2884* (2013.01); *C07K 16/2896* (2013.01); *A61K 9/006* (2013.01); *A61K 9/0043* (2013.01)

(58) Field of Classification Search
CPC .............. A61K 31/728; A61K 47/6849; A61K 47/6875; A61K 47/6903; A61K 47/6907; A61K 47/6925; A61K 47/6929; A61K 9/1075; A61P 9/10; A61P 9/14; C07K 16/2884; C07K 16/2896
See application file for complete search history.

(56) References Cited

U.S. PATENT DOCUMENTS

| | | |
|---|---|---|
| 6,168,804 B1 | 1/2001 | Samuel et al. |
| 6,258,378 B1 | 7/2001 | Schneider et al. |
| 6,451,338 B1 | 9/2002 | Gregoriadis et al. |
| 2008/0286372 A1* | 11/2008 | Pacetti ................. A61K 9/0019 424/493 |
| 2017/0080006 A1 | 3/2017 | Tunac et al. |

FOREIGN PATENT DOCUMENTS

CA 2252055 A1 10/1997

OTHER PUBLICATIONS

Becker et al., "Therapeutic strategies targeting the endothelial glycocalyx: acute deficits, but great potential", 2010, Cardiovascular Research, vol. 87, pp. 300-310. (Year: 2010).*
Reitsma, Sietze, et al., "The endothelial glycocalyx: composition, functions, and visualization." Pflügers Archiv-European Journal of Physiology 454.3 (2007): 345-359.
Chappell, Daniel, et al., "Antithrombin reduces shedding of the endothelial glycocalyx following ischaemia/reperfusion." Cardiovascular research 83.2 (2009): 388-396.
Becker, Bernhard F., et al. "Therapeutic strategies targeting the endothelial glycocalyx: acute deficits, but great potential." Cardiovascular research 87.2 (2010): 300-310.
Broekhuizen, Lysette N., et al., "Effect of sulodexide on endothelial glycocalyx and vascular permeability in patients with type 2 diabetes mellitus." Diabetologia 53.12 (2010): 2646-2655.
Coccheri, Sergio, et al. "Development and use of sulodexide in vascular diseases: implications for treatment." Drug design, development and therapy 8 (2014): 49-65.
Giantsos-Adams, Kristina M., et al. "Heparan sulfate regrowth profiles under laminar shear flow following enzymatic degradation." Cellular and molecular bioengineering 6.2 (2013): 160-174.
Giantsos-Adams, Kristina M., et al. "Study of the therapeutic benefit of cationic copolymer administration to vascular endothelium under mechanical stress." Biomaterials 32.1 (2011): 288-294.
Henry, Charmaine BS, et al. "Permeation of the luminal capillary glycocalyx is determined by hyaluronan." American Journal of Physiology-Heart and Circulatory Physiology 277.2 (1999): H508-H514.
Jacob, Matthias, et al. "Contrasting effects of colloid and crystalloid resuscitation fluids on cardiac vascular permeability." Anesthesiology: The Journal of the American Society of Anesthesiologists 104.6 (2006): 1223-1231.
Jacob, Matthias, et al. "Albumin augmentation improves condition of guinea pig hearts after 4 hr of cold ischemia." Transplantation 87.7 (2009): 956-965.
Potter, Daniel R., et al. "The recovery time course of the endothelial cell glycocalyx in vivo and its implications in vitro." Circulation research 104.11 (2009): 1318-1325.
Song, J. W., et al. "Therapeutic restoration of endothelial glycocalyx in sepsis." Journal of Pharmacology and Experimental Therapeutics 361.1 (2017): 115-121.

(Continued)

*Primary Examiner* — Michael B. Pallay
(74) *Attorney, Agent, or Firm* — Leason Ellis LLP

(57) ABSTRACT

The present disclosure relates to compositions and methods for restoring endothelial glycocalyx. Exemplary compositions include nanoparticle compositions of preassembled glycocalyx.

16 Claims, 21 Drawing Sheets
(11 of 21 Drawing Sheet(s) Filed in Color)

(56) References Cited

OTHER PUBLICATIONS

Van Den Berg, Bernard M., et al. "Glycocalyx and endothelial (dys) function: from mice to men." Pharmacological Reports 58 (2006): 75-80.
Ziolkowski, Andrew F., et al. "Heparan sulfate and heparanase play key roles in mouse β cell survival and autoimmune diabetes." The Journal of clinical investigation 122.1 (2012): 132-141.
Sanja Cabric, et al. "A New Method for Incorporating Functional Heparin onto the Surface of Islets of Langerhans" Tissue Engineering: Part C, vol. 14, No. 2, 2008; pp. 141-147.
Sofia Nordling, et al. "Enhanced protection of the renal vascular endothelium improves early outcome in kidney transplantation: Preclinical investigations in pig and mouse" Scientific Reports (2018) 8:5220; pp. 1-9.
James R. Wodicka, et al. "Development of a Glycosaminoglycan Derived, Selectin Targeting Anti-Adhesive Coating to Treat Endothelial Cell Dysfunction" Pharmaceuticals 2017, 10, 36; pp. 1-19.
Nolan B. Holland, et al. "Biomimetic engineering of non-adhesive glycocalyx-like surfaces using oligosaccharide surfactant polymers" Nature, vol. 392, Apr. 23, 1998, pp. 799-801.
Eddie T. Chiang, et al. "Protective Effects of High-Molecular Weight Polyethylene Glycol (PEG) in Human Lung Endothelial Cell Barrier Regulation: Role of Actin Cytoskeletal Rearrangement" Microvasc Res. Mar. 2009; 77(2): pp. 174-186.
S. Bertuglia, et al. "Polyethylene glycol and a novel developed polyethylene glycol-nitric oxide normalize arteriolar response and oxidative stress in ischemia-reperfusion" Am J Physiol Heart Circ Physiol 291: 2006; pp. H1536-H1544.

* cited by examiner

Figure 5
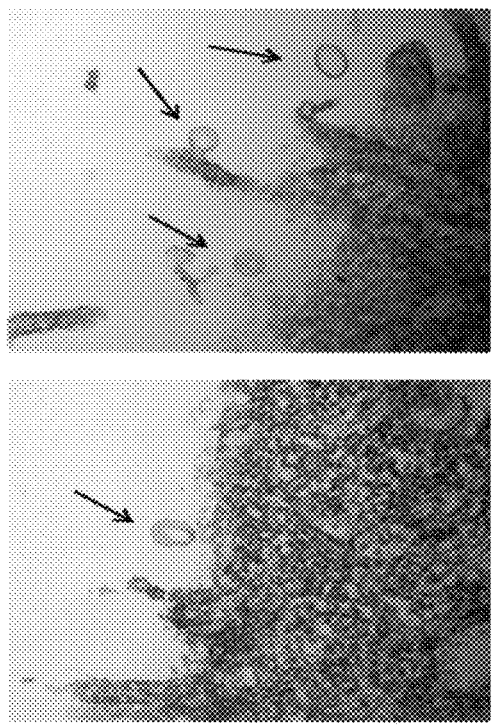
Images of RMVEC Pretreated with Heparanase and Treated with Liposomes
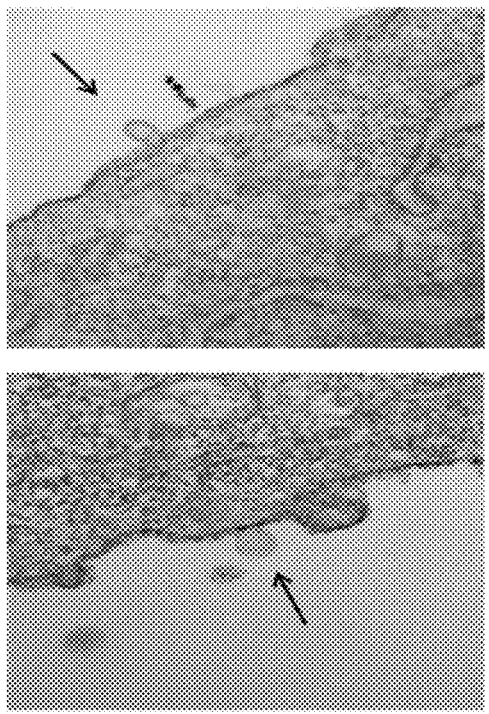
Images of Intact RMVEC with Attached Liposomes AFM nanoindentation studies of cultured renal microvascular endothelial cells isolated from db/db mice

COMPOSITIONS AND METHODS FOR RESTORING ENDOTHELIAL GLYCOCALYX

This application claims priority to U.S. provisional application No. 62/563,297, filed on Sep. 26, 2017, the contents of which are hereby incorporated by reference in their entirety.

FIELD OF THE INVENTION

The present disclosure relates to compositions and methods for restoring endothelial glycocalyx. Exemplary compositions include nanoparticle carriers of preassembled glycocalyx and related methods for treating diseases involving disruption of the glycocalyx, inflammation, and oxidative damage.

BACKGROUND OF THE INVENTION

The existence of the glycocalyx, a thin layer at the endothelial surface was discovered about 40 years ago (1966. Fed Proc 25:1773-1783). However, the significance of this structure was not recognized, partly because it is destroyed upon conventional tissue fixation and not seen in most light microscopic examinations. The glycocalyx is a protective lining at the surface of the endothelium found in every healthy blood vessel; it is made of proteoglycan, a complex network of protein (glycoprotein) and disaccharide sugar (glycosaminoglycan). This complex network (originating from plasma and vessel wall) forms a dynamic layer between the flowing blood and the endothelium, continuously changing in thickness depending on shear or blood flow pressure. Thus, the shear generated by blood flow regulates the balance between biosynthesis and shedding of the various glycocalyx components. The core protein groups of this layer are syndecans and glypicans promiscuously bound with different glycosaminoglycan including heparan sulfate, chondroitin sulfate, dermatan sulfate, keratan sulfate, and hyaluronan (or hyaluronic acid) bound to CD44. In the vasculature, heparan sulfate represents roughly 50-90% of the total amount of proteoglycans followed by chondroitin sulfate with a typical ratio of 4:1, respectively (2007. Pflugers Arch; 454: 345-359).

Diverse pathologic conditions are associated with the loss of endothelial glycocalyx (EG), the outermost layer represented by a meshwork of scaffolding proteoglycans with covalently bound glycoproteins and glycosaminoglycans. Glycocalyx serves critically important functions of regulation of vascular permeability and coagulation, traffic of leukocytes, mechanosensing and flow-induced nitric oxide production. Hence, when glycocalyx is lost or defective, all the above functions become dysregulated. Attempts to restore glycocalyx are a few and only partially curative.

There remains a need for a method of restoring and/or maintaining the integrity of the protective glycocalyx lining of the endothelial vessel wall.

SUMMARY OF THE INVENTION

The present invention provides for a composition for treating multiple disease causes including a glycocalyx restoring and maintaining compound.

In certain embodiments, the disclosure provides a composition comprising: a proteoglycan, heparan sulfate, and hyaluronic acid, formulated as a nanoparticle.

In certain embodiments, the proteoglycan is syndecan or glypican.

In additional embodiments, the proteoglycan comprises syndecan-1, syndecan-2, syndecan-3 or syndecan-4, or mixtures thereof.

In yet additional embodiments, the composition further comprises an antibody for targeting the composition to the endothelial glycocalyx. In yet additional embodiments, the antibody comprises anti-CD31, anti-CD117 (C-Kit), or anti-CD44 antibody.

In further embodiments, the nanoparticle comprises micelles, liposomes, polymersomes, hydrogel particles or polymer particles. In yet additional embodiments, the nanoparticle has a maximum linear dimension of 1000 nanometers.

In further embodiments, the composition further comprises a drug or active agent. In additional embodiments, the active agent is sulodexide.

In yet additional embodiments, the nanoparticle is a liposome and the liposome is optionally PEGylated.

In yet additional embodiments, the syndecan is labeled with a detectable label.

In additional embodiments, the present disclosure provides a method for restoring endothelial glycocalyx in desired membranes in a patient in need thereof, comprising administering an effective amount of the composition described herein to the patient.

In certain embodiments, the composition further comprises CD44 which specifically targets the desired membranes for endothelial glycocalyx restoration. It is noted that CD44 is optional, and may be used to provide a receptor for hyaluronic acid.

In additional embodiments, the present disclosure provides a method of treating multiple disease causes, by administering a glycocalyx restoring and maintaining compound to an individual, restoring the glycocalyx, flow-induced vasodilation due to nitric oxide (NO) production and potentially reversing inflammation, and reversing oxidative damage. The present disclosure also provides for a method of treating cardiovascular disease (CVD) by administering a glycocalyx restoring and maintaining compound to an individual suffering from CVD thereby restoring the glycocalyx and microcirculation, reversing inflammation, and reversing oxidative damage.

The present disclosure provides for a method of restoring the glycocalyx by administering the glycocalyx restoring and maintaining compound to an individual and restoring the glycocalyx.

The present disclosure also provides for a method of reversing inflammation by administering the glycocalyx compound to an individual, reversing inflammation, and restoring the glycocalyx.

The present disclosure also provides for a method of reversing oxidative damage by administering the glycocalyx compound to an individual, reversing oxidative damage, and restoring the glycocalyx.

The present disclosure also provides for a method of treating any disease involving a membrane that has a glycocalyx, by administering the glycocalyx compound to an individual, restoring the glycocalyx of the membrane, reversing inflammation, and reversing oxidative damage.

In yet additional embodiments, the treatment restores the glycocalyx, reverses inflammation, and reverses oxidative damage in the targeted membranes.

In further embodiments, the administration is by injection. In yet additional embodiments, the administration is nasal, sublingual, percutaneous, or intestinal.

BRIEF DESCRIPTION OF THE DRAWINGS

The patent or application file contains at least one drawings executed in color. Copies of this patent or patent application publication with color drawing(s) will be provided by the Office upon request and payment of the necessary fee.

FIG. 5 shows images of electron microscopy of renal microvascular endothelial cells RMVEC, intact (top) or heparanase-treated (bottom), with attached liposomes with preassembled EG. RMVEC were cultured on Thermanox, treated with restorative glycocalyx nanoliposomes ($12.9 \times 10^8$/ml), fixed and stained with 1.5% uranyl acetate. All samples were viewed in a JEOL JSM 1400 TEM operating at 100 Kv. Images were captured on a Veleta 2K×2K CCD camera (EMSIS GmbH). Note also the near-disappearance of EG (an electron-dense cell outline in control) after heparanase treatment. Attachment of liposomes to cells with degraded EG increased 6-fold compared to intact cells.

DETAILED DESCRIPTION

Figure 1:
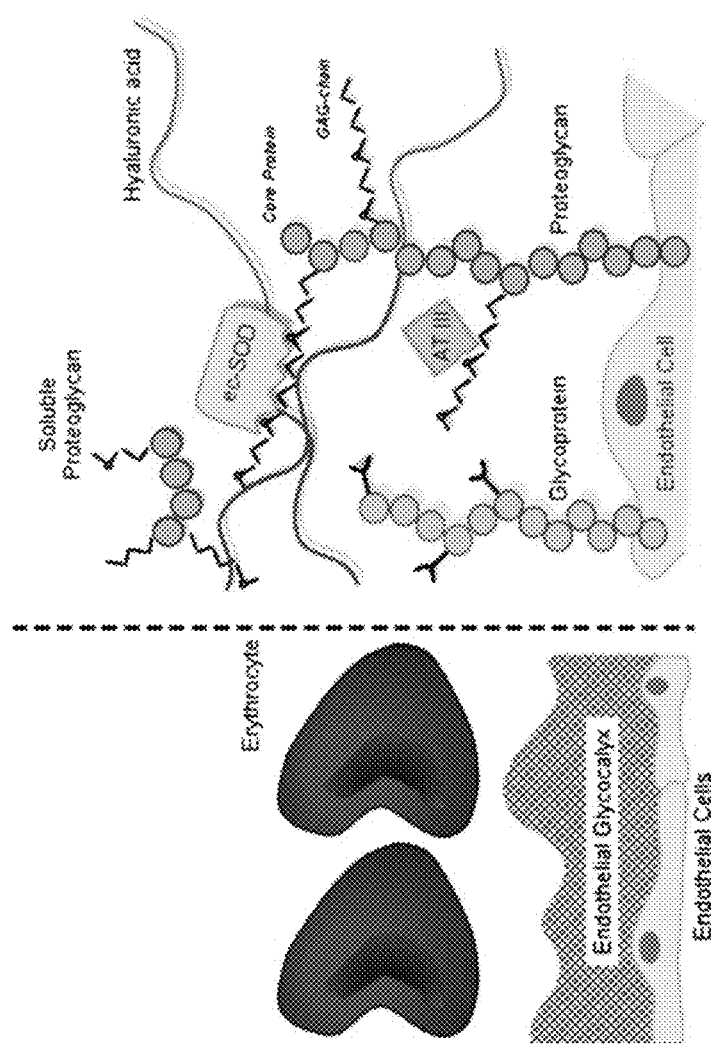
FIG. 1 is a schematic representation of the endothelial glycocalyx. In the left panel: The endothelial glycocalyx can be observed in vivo as a red blood cell exclusion zone, located on the luminal side of the vascular endothelium. It consists of membrane bound and soluble molecules. In the right panel: Components of the endothelial glycocalyx. Bound to the endothelial membrane are proteoglycans, with long unbranched glycosaminoglycan side-chains (GAG-chain) and glycoproteins, with short branched carbohydrate side-chains. Incorporated in and on top of this grid are plasma and endothelium derived soluble components, including hyaluronic acid and other soluble proteoglycans (e.g., thrombo modulin) and various proteins, such as extracellular superoxide dismutase (ec-SOD) and antithrombin III (AT III). Together, these components form the endothelial glycocalyx that functions as a barrier between blood plasma and the endothelium and exerts various roles in plasma and vessel wall homeostasis. Note that this figure is not drawn to scale, but shows the various components of the EG.

The present invention relates to methods and compositions for treating diseases involving disruption of the glycocalyx, inflammation, and oxidative damage. In certain embodiments, the present invention relates to methods and compositions for treating cardiovascular disease associated with such conditions involving disruption of the glycocalyx.

Exemplary compositions include nanoparticle carriers of preassembled glycocalyx and related methods for treating diseases involving disruption of the glycocalyx, inflammation, and oxidative damage. In certain embodiments, the composition comprises a proteoglycan, heparan sulfate, and hyaluronic acid, which are covalently bound and formulated as a nanoparticle. In certain embodiments, the composition may further include a targeting moiety which may be any of the following: anti-CD31, anti-CD117 (C-Kit), or anti-CD44 antibody.

In certain embodiments, the present disclosure includes nanoparticle compositions of preassembled glycocalyx for restoring glycocalyx functions or preventing glycocalyx damage and related methods. The compositions and therapeutic methods described herein encompass all pathologies where glycocalyx damage or this function may be etiologically cause of many pathologies such as: vascular disease, septic states, atherosclerosis syndrome, inflammation states and disease related to ischemia, peritoneal impairment, myocardial infarction, cerebrovascular events, alteration of enzymatic glycosylation in diabetes, kidney injury, intestinal disease as ulcerous colitis conditions, pneumoconiosis involving alteration of metabolic activity of pulmonary endothelium and other similar conditions.

While not being bound by theory, an aspect of the present glycocalyx restoring compositions is that the composition exhibits fusogenic properties, that is it fuses into the endothelium e.g., it fuses with the plasma membrane of endothelial or any other cell (contrasted with a composition that merely binds to the cell surface).

The glycocalyx can also be found on the apical portion of the microvilli within the digestive tract, especially within the small intestine. It creates a meshwork 0.3 micrometers thick and consists of acidic mucopolysaccharides and glycoproteins that project from the apical plasma membrane of epithelial absorptive cells It provides additional surface for adsorption and includes enzymes secreted by the absorptive cells that are essential for the final steps of digestion of proteins and sugars. Each cell is surrounded by a glycocalyx. Cells form a glycocalyx layer of a tissue's surface and form a barrier. Once disrupted, the underlying cell is susceptible to disruption and immune attack by macrophages and the like. The glycocalyx of endothelial cells, such as the endometrium, the inner surface of the lungs, the microvilli of the kidney, the pancreas, etc., form a cellular seal that cannot be disrupted.

Other generalized functions affected by status of glycocalyx include protection (it cushions the plasma membrane and protects it from chemical injury), immunity to infection (it enables the immune system to recognize and selectively attack foreign organisms), defense against cancer (changes in the glycocalyx of cancerous cells enable the immune system to recognize and destroy them), transplant compatibility (it forms the basis for compatibility of blood transfusions, tissue grafts, and organ transplants), cell adhesion (it binds cells together so that tissues do not fall apart), inflammation regulation (glycocalyx coating on endothelial walls in blood vessels prevents leukocytes from rolling/binding in healthy states), fertilization (it enables sperm to recognize and bind to eggs), and embryonic development (it guides embryonic cells to their destinations).

The glycocalyx is currently recognized as a key structure for maintaining vascular wall integrity and proper function of many organs. Disruptions in the glycocalyx can be due to oxidative stress, ischemia-reperfusion, high blood glucose, or impaired fluid flow. A thick glycocalyx indicates the absence of plaque, found at straight flow and high shear areas. A thin glycocalyx promotes plaque buildup, especially where there is whirlpool blood flow with low shear in vascular bends. Plaques are essentially patches that cover tiny gaps to maintain osmotic balance of membranes. The tiny gaps in the membrane leak electrolytes both into (Na+Cl−, Ca+, $HCO_3$) and out (K+, $PO4−$, Mg+) of cells which can lead to a number of conditions. Disruptions can also be caused by the presence of oxidants or debris in adjacent fluid.

It is noted that intact glycocalyx may vary in height/thickness from about 0.1 to about 2 μm. Thus, an aspect of the presently described restorative glycocalyx nanoliposome compositions is that they can function to restore damaged of diseased glycocalyx (e.g. too thin or disrupted glycocalyx) to a more normal height/thickness of from 0.1 to about 2 μm.

Any disruption or decrease in thickness of the glycocalyx can result in many different conditions, including chronic vascular disease (2010. Cardiovascular Research. Volume 87, Issue 2 pp. 300-310). For example, chronic stagnant blood flow, common in bifurcated sections of the arteries, triggers glycocalyx shedding and plaque formation. In the heart, disrupted glycocalyx in the coronaries result in poor blood flow (coronary perfusion); at the arteriolar level, a damaged glycocalyx slows down blood flow and decreases nitric oxide (NO) production creating constrictive vessel; and, at the capillary level, disrupted glycocalyx reduces blood flow to tissues or muscles. In addition, the glycocalyx harbors a wide array of enzymes that regulate proper blood flow including superoxide dismutase (SOD), an enzyme which neutralizes reactive oxygen species; antithrombin (AT-III), a natural anticoagulant (blood thinner); and, lipoprotein lipase (LPL), an enzyme that releases triglycerides from chylomicrons and very low-density lipoproteins (VLDL) for energy.

In case of cardiac ischemia/reperfusion injury (heart muscle damage due to blood flow obstruction, then re-establishment of blood supply), disrupted glycocalyx results in coronary constriction, poor blood flow, and edema. However, pre-treatment of the heart with antithrombin reduces glycocalyx shedding and restores coronary functions (2009. Cardiovascular Research. Volume 83, Issue 2Pp. 388-396). Other more general consequences of a disrupted glycocalyx include osmotic gradient shifts, leakage between cells (such as vascular, kidney, and lung cells), macrophage infiltration and inflammation, and tissue dysfunction. Eventually, glycocalyx dysfunction can lead to blockage of flow in vasculature, the kidneys, the pancreas, and other organs and tissue.

Abbreviations

AKI: acute kidney injury;
EG: endothelial glycocalyx;
GAG's: glycosaminoglycans
HA: Hyaluronic acid
HS: heparan sulfate;
NO: nitric oxide;
ROS: reactive oxygen species;
SOD: superoxide dismutase.

Definitions

"Disrupting" or "disruption of" the glycocalyx as used herein refers to any process or disease state that affects the glycocalyx such that it is not functioning normally. Disruption can be caused by inflammation or oxidation in the body. Disruption can cause the glycocalyx to thin and lose its component proteoglycans.

"Inflammation" as used herein refers to a protective response of tissue to injury or destruction in order to eliminate or cordon off any injurious agent and the injured tissue and initiate tissue repair. Inflammation can cause pain, heat, redness, swelling, and loss of function. Inflammatory mediators (cytokines and chemoattractants) can cause shedding of the glycocalyx. Inflammation can also cause leukocytes to degranulate enzymes that can degrade the glycocalyx.

"Oxidative damage", "oxidative stress", or "oxidation" as used herein refers to an imbalance of reactive oxygen species (ROS) and the body's ability to detoxify reactive intermediates and repair damage caused by ROS. Inflammation can cause the release of ROS. The presence of ROS can cause significant damage to cell structures, including the glycocalyx.

"Antioxidant" as used herein refers to a molecule that inhibits the oxidation of other molecules and is able to neutralize or eliminate ROS.

The present invention provides for a composition for treating multiple disease causes of a glycocalyx restoring and maintaining compound. The composition preferably treats disruption of the glycocalyx, inflammation, and oxidative damage. The composition can also treat any one of these causes individually. The glycocalyx restoring and maintaining compound can be any suitable compound that is able to perform these functions in the body.

Pharmaceutical compositions of the present invention may be presented in unit dose forms containing a predetermined amount of active ingredient per unit dose. Such a unit may contain, for example, 5 g to 1 g, preferably 1 mg to 700 mg, more preferably 5 mg to 100 mg of the glycocalyx restoring compound described herein, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art. Exemplary dosage includes 5 mg/kg in mice.

Pharmaceutical compositions of the present invention may be adapted for administration by any appropriate route, for example by the oral (including buccal or sublingual), inhaled, nasal, ocular, or parenteral (including intravenous and intramuscular) route. Such compositions may be prepared by any method known in the art of pharmacy, for example by bringing into association the active ingredient with the carrier(s) or excipient(s).

As used herein, "nanoparticle" refers to a microscopic particle, composed of one or more polymers, whose size in nanometers (nm) includes a maximum linear dimension of less than 1000 nanometers. As used herein, linear dimension refers to the distance between any two points on a nanoparticle as measured in a straight line. Nanoparticles of the present invention can be irregular, oblong, spindle, rod, discoid, pancake, cylindrical, red blood cell-like, spherical or substantially spherical in shape as long as their shape and size allow binding interactions with platelets.

As used herein, "substantially spherical" refers to a shape that is not perfectly spherical but has a generally spherical shape, e.g., an ellipsoid.

As used herein, a "polymer" refers to a molecule(s) composed of a plurality of repeating structural units connected by chemical bonds.

Several types and configurations of nanoparticles are encompassed by the present invention. For example, nanoparticles may be composed of a range of materials including, but not limited to, a biostable polymer, a bioabsorbable polymer or a combination thereof. Biostable refers to polymers that are not degraded in vivo, i.e., are not biodegradable. The terms bioabsorbable, biodegradable, and bioerodable, as well as absorbed, degraded and eroded are used interchangeably (unless the context shows otherwise) and refer to polymers that are capable of being degraded or absorbed after being delivered to a disease locale in a patient, e.g., when exposed to bodily fluids such as blood, and that can be gradually resorbed, absorbed, and/or eliminated by the body.

Nanoparticles of the present invention can include biodegradable and bioerodable materials that, after delivery, biodegrade or bioerode within 1.0 second to 100 hours, within 10.0 seconds to 10 hours or within 1 minute to 1 hour. Methods of forming nanoparticles with known degradation rates are known to those skilled in the art; see for example U.S. Pat. No. 6,451,338 to Gregoriadis et al., U.S. Pat. No. 6,168,804 to Samuel et al. and U.S. Pat. No. 6,258,378 to Schneider et al., which are hereby incorporated by reference in their entirety.

Suitable nanoparticles include micelles, liposomes, polymersomes, hydrogel particles and polymer particles.

As used herein, a "micelle" refers to a supramolecular aggregate of amphipathic molecules in an aqueous solution. Amphiphilic molecules have two distinct components, differing in their affinity for a solute, most particularly water. The part of the molecule that has an affinity for water, a polar solute, is said to be hydrophilic. The part of the molecule that has an affinity for non-polar solutes such as hydrocarbons is said to be hydrophobic. When amphiphilic molecules are placed in an aqueous solution the hydrophilic moiety seeks to interact with the water while the hydrophobic moiety seeks to avoid the water, i.e., they aggregate at the surface of the water. Amphiphilic molecules that have this effect are known as "surfactants." When the CMC is reached surfactant molecules will self-assemble into spheres with the hydrophilic ends of the molecules facing out, that is, in contact with the water forming the micelle corona and with the hydrophobic "tails" facing toward the center of the of the sphere.

As used herein, a "liposome" refers to a compartment that is completely enclosed by a bilayer typically composed of phospholipids. Liposomes can be prepared according to standard techniques known to those skilled in the art. For example, without limitation, suspending a suitable lipid, e.g., phosphatidyl choline, in an aqueous medium followed by sonication of the mixture will result in the formation of liposomes. Alternatively, rapidly mixing a solution of lipid in ethanol-water, for example, by injecting a lipid through a needle into an agitated ethanol-water solution can form lipid vessicles. Liposomes can also be composed of other amphiphilic substances, e.g., shingomyelin or lipids containing poly(ethylene glycol) (PEG).

As used herein, a "polymersome" refers to di- or tri-block copolymers that are modified to form bilayer structures similar to liposomes. Depending on the length and composition of the polymers in the block copolymer, polymersomes can be substantially more robust that liposomes. In addition, the ability to control the chemistry of each block of the block copolymer permits tuning of the polymersome's composition to fit the desired application. For example, membrane thickness, i.e., the thickness of the bilayer structure, can be controlled by varying the chain length of the individual blocks. Adjusting the glass transition temperatures of the blocks will affect the fluidity and therefore the permeability of the membrane. Even the mechanism of agent release can be modified by altering the nature of the polymers.

Polymersomes can be prepared by dissolving the copolymer in an organic solvent, applying the solution to a vessel surface, and then removing the solvent, which leaves a film of the copolymer on the vessel wall. The film is then hydrated to form polymersomes. Dissolving the block copolymer in a solvent and then adding a weak solvent for one of the blocks, will also create polymersomes. Other means of preparing polymersomes are known to those skilled in the art and are within the scope of this invention.

Polymersomes can be used to encapsulate bioactive agents by including the bioactive agent in the water used to rehydrate the copolymer film. Osmotically driving the bioactive agent into the core of preformed polymersomes, a process known as force loading, may also be employed. Using a double emulsion technique, polymersomes of relative monodispersivity and high loading efficiency are possible. The technique involves using microfluidic technology to generate double emulsions comprising water droplets surrounded by a layer of organic solvent. These droplet-in-a-drop structures are then dispersed in a continuous water phase. The block copolymer is dissolved in the organic solvent and self-assembles into proto-polymersomes on the concentric interfaces of the double emulsion. Completely evaporating the organic solvent from the shell yields the actual polymersomes. This procedure allows fine control over the polymersome size. In addition, the ability to maintain complete separation of the internal fluids from the external fluid throughout the process allows extremely efficient encapsulation.

As used herein, a "hydrogel particle" refers to a cross-linked network of polymer chains that is absorbent but stable in an aqueous environment. Hydrogel particles can be used to encapsulate bioactive agents by methods known to those skilled in the art.

As used herein, a "polymer particle" refers to a solid or porous particle, in contrast to the shell structure of liposomes and polymersomes and the relatively open structures of hydrogel particles. Methods for adhering a bioactive agent to the surface of or integrating a bioactive agent into the structure of a polymer particle are known to those skilled in the art.

Polymers that may be used to prepare nanoparticles of this invention include, but are not limited to, poly(N-acetyglucosamine) (Chitin), Chitosan, poly(3-hydroxyvalerate), poly (lactide-co-glycolide), poly(3-hydroxybutyrate), poly(4-hydroxybutyrate), poly(3-hydroxybutyrate-co-3-hydroxyvalerate), polyorthoester, polyanhydride, poly (glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly (glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrin glue, fibrinogen, cellulose, starch, collagen and hyaluronic acid, elastin and hyaluronic acid), polyurethanes, silicones, polyesters, polyolefins, polyisobutylene and ethylene-alphaolefin copolymers, acrylic polymers, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates including tyrosine-based polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, carboxymethyl cellulose, fullerenes and lipids.

As used herein, "operatively coupled" refers to the attachment of a desired group or datable agent (e.g. fluorescent label, gold label or any other datable label) to the surface of a nanoparticle through either direct or indirect means. For example, it is possible for a desired group to be directly attached to the surface of the nanoparticle by a portion of the desired group itself. Alternatively, it is possible that the desired group is attached to the surface of the nanoparticle via an intermediate component that couples the desired group with the surface of the nanoparticle. Such intermediate components are often referred to as linkers. Linkers are di-functional molecules that can have one moiety that chemically attaches to a nanoparticle and a second moiety that chemically attaches to a functional group. Any number of intermediate components are encompassed by the present invention, and are known to those skilled in the art.

Functional groups can be localized to the surface of the nanoparticle by anchoring them to the surface. For example, a functional group with affinity for endothelium can be covalently bonded to the hydrophilic end of an amphiphilic molecule, such as a phospholipid with a hydrophilic spacer region coupled to its headgroup, or an amphiphilic block co-polymer, such as PEG-PLA. These anchored functional groups may then be localized to the surface of a nanoparticle by co-incubation of the groups with pre-made nanoparticles, or by including these groups during the nanoparticle formulation process, methods of which are known to those skilled in the art.

As used herein, an "aptamer" refers to an oligo nucleic acid that has binding affinity for a specific target, e.g., without limitation, a protein, a nucleic acid, a specific whole cell or a particular tissue. Aptamers can be obtained by in vitro selection from a large random sequence pool of nucleic acids, although natural aptamers are also encompassed by the present invention. Other methods of producing aptamers are known to those skilled in the art in certain embodiments, aptamers may be incorporated into The targeting moiety can be an affibody or an antibody, including anti-CD31, anti-CD117 (C-Kit), or anti-CD44 antibody.

As used herein, an "affibody" refers to a relatively small synthetic protein molecule that has high binding affinity for a target protein. Affibodies are composed of a three-helix bundle domain derived from the IgG-binding domain of staphylococcal protein A. The protein domain consists of a 58 amino acid sequence, with 13 randomized amino acids affording a range of affibody variants. Despite being significantly smaller than an antibody (an affibody weighs about 6 kDa while an antibody commonly weighs about 150 kDa), an affibody molecule works like an antibody since it's binding site is approximately equivalent in surface area to the binding site of an antibody.

As used herein, a "prophylactically effective" amount is an amount of a substance effective to prevent or to delay the onset of a given pathological condition in a subject to which the substance is to be administered. A prophylactically effective amount refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, a "therapeutically effective" amount is an amount of a substance effective to treat, ameliorate or lessen a symptom or cause of a given pathological condition in a subject suffering therefrom to which the substance is to be administered.

In one embodiment, the therapeutically or prophylactically effective amount is from about 1 mg of agent/kg subject to about 1 g of agent/kg subject per dosing. In another embodiment, the therapeutically or prophylactically effective amount is from about 10 mg of agent/kg subject to 500 mg of agent/subject. In a further embodiment, the therapeutically or prophylactically effective amount is from about 50 mg of agent/kg subject to 200 mg of agent/kg subject. In a further embodiment, the therapeutically or prophylactically effective amount is about 100 mg of agent/kg subject. In still a further embodiment, the therapeutically or prophylactically effective amount is selected from 50 mg of agent/kg subject, 100 mg of agent/kg subject, 150 mg of agent/kg subject, 200 mg of agent/kg subject, 250 mg of agent/kg subject, 300 mg of agent/kg subject, 400 mg of agent/kg subject and 500 mg of agent/kg subject.

"Treating" or "treatment" of a state, disorder or condition includes:
 (1) preventing or delaying the appearance of clinical symptoms of the state, disorder, or condition developing in a person who may be afflicted with or predisposed to the state, disorder or condition but does not yet experience or display clinical symptoms of the state, disorder or condition; or
 (2) inhibiting the state, disorder or condition, i.e., arresting, reducing or delaying the development of the disease or a relapse thereof (in case of maintenance treatment) or at least one clinical symptom, sign, or test, thereof; or
 (3) relieving the disease, i.e., causing regression of the state, disorder or condition or at least one of its clinical or sub-clinical symptoms or signs.

The benefit to a subject to be treated is either statistically significant or at least perceptible to the patient or to the physician.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopeias for use in animals, and more particularly in humans.

"Patient" or "subject" refers to mammals and includes human and veterinary subjects. Certain veterinary subjects may include avian species.

This invention will be better understood from the Experimental Details, which follow. However, one skilled in the art will readily appreciate that the specific methods and results discussed are merely illustrative of the invention as described more fully in the claims that follow thereafter.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Results

The natural structure-functional restoration of EG is sluggish. It has previously been determined that after degradation of EG with either hyaluronidase, heparanase III or TNF-α the restoration of hydrodynamically relevant EG in vivo requires ~7 days (1). In cultured endothelial cells, restoration of HS after its enzymatic degradation requires 12 h under laminar flow conditions and 20 h under static conditions (2). Attempts to accelerate EG restoration have been entertained. Administration of antioxidants, like N-acetylcysteine (3), was used to prevent EG shedding during hyperglycemia. However, considering the fact that extracellular superoxide dismutase (SOD) is heavily intercalated in the EG, it is questionable whether effects of antioxidants are really preventive or rather they act when EG has been degraded and subsequently the normally present SOD barrier has been lost and thus replaced by an exogenous antioxidant. An alternative strategy is represented by systemic use of high molecular weight HA (HMW-HA). Studies have demonstrated that supplemental infusion of HA and chondroitin sulfate accelerates restoration of EG (4). A similar approach uses heparan sulfate or its analog, Sulodexide (an 8:2 mixture of fast-moving heparin fraction and dermatan sulfate, respectively (5), to improve EG in diabetes, though clinical trials showed a limited success (6). Based on the evolving appreciation of the role played by sheddases in the degradation of EG, Becker et al (7) advocate inhibitors of inflammation, antithrombin and inhibitors of metalloproteases as potential means to reduce degradation of EG in clinical settings. Therapeutic benefits of cationic copolymer administration to vascular endothelium under mechanical stress were reported (8). All above-proposed strategies, however, are far from being complete and long-lasting due to many factors such as degradation, lack of targeting, etc. Most importantly, they supply only individual components of EG, while it has been shown that individual components of EG were ineffective in a septic model and the testedcocktail was not more effective than Sulodexide alone (11). There is data demonstrating that a non-cleavable competitive inhibitor of heparanase, PI-88, a sulfated phosphomanno-oligosaccharide mimetic of heparan sulfate, protects insulin-producing beta-cells and delays development of type I diabetes in NOD mice (10). It is not known how protective this inhibitor is in vascular endothelial cell under control and pathologic conditions. The use of a complex substance with the properties of inhibition of enzymes degrading glycocalyx (sulodexide) was previously tested and also found to be deficient in restoring glycocalyx (11).

However, the composition described herein has advantages of targeted delivery of the entire pre-assembled glycocalyx rather than individual building blocks.

Additionally, the pre-assembled glycocalyx compositions described herein has advantages of targeted delivery of the entire pre-assembled glycocalyx rather than individual building blocks. It is expected that the pre-assembled glycocalyx compositions described herein will have therapeutic effects on many conditions which impact the vasculature, as noted in Table 3.

Figure 2:
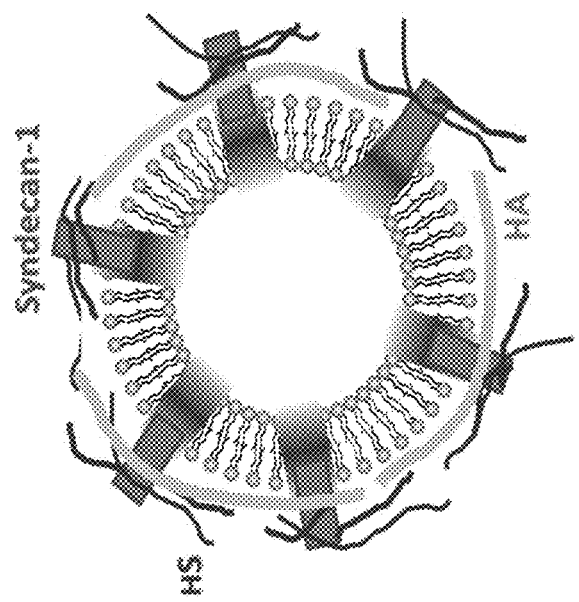
FIG. 2 is a schema showing a representative idealized nanoliposomal construct containing the EG-substituting portion (combination of Syndecan-1, HS and HA).

While not wishing to be bound by theory, the glycocalyx composition and related methods described herein are based in part of the following 1) to conjugate a section of "pre-assembled glycocalyx" (e.g. a proteoglycan, heparan sulfate, and hyaluronic acid, which are covalently bound or bound by van der Waal's forces) to one pole of nanoparticles (liposomes etc.—any suitable material that can carry these components) and 2) optional targeting of these nanoparticles to the mature endothelial and endothelial stem cells. In certain embodiments, there are "breakable bridges" between the nanoparticles and prefabricated glycocalyx, which provide a benefit: when the particle becomes attached and its endocytosis initiated, the dandelion-like (the combination of a syndecan, HS, and HA) portion of glycocalyx is ejected from it to form a restored glycocalyx. This structure is schematically depicted in FIG. 2.

It is noted that the glycosaminoglycan (GAGS) components of the proteoglycan can be covalently bound, or bound by van der Waal's forces.

Regeneration of glycocalyx occurs by and large based on the fusion of liposomes with the plasma membrane. Thus, it is expected that the glycocalyx composition described herein, when administered to a patient, will be targeted to and fuse with the endothelium to restore a normal glycocalyx in any number of conditions.

Optional targeting can be achieved by adding an antibody to CD31, to the composition or another targeting antibody such as anti-CD117 (C-Kit), or anti-CD44 antibody.

In preparing the nanoliposomes the following options may be included:
1) Conjugation with an antibody to CD31 and syndecan-1 (or syndecan-4);
2) Hyaluronic acid (HA) and heparan sulfate (HS) may be added to the composition later and spontaneously bind to syndecans.
3) All other components are optional, including bioactive agents and further targeting agents/moieties.

Exemplary glycocalyx formulation (A) preassembled as nanoparticles: A syndecan-1-conjugated, DiI-labeled (for monitoring using fluorescence microscopy) nanoliposome composition (referred to herein as a restorative glycocalyx nanoliposome composition) has been synthesized and formulated. Below is its chemical composition:

The total lipid concentration of formulation A is 1.71 mM. The liposomes are 100 nm in size, thus each liposome is composed of 80,000 lipid molecules and there are a total of 12.9 trillion ($12.9^{12}$) liposome particles per ml of solution containing formulation (A) preassembled as nanoparticles. The concentration of Syndecan is about 0.73 μM which is equal to $4.4^{14}$ molecules of Syndecan (440 Trillion Syndecan molecules). Thus, there are approximately or about 34 molecules of Syndecan incorporated into each liposome particle.

This preparation has been reacted with heparan sulfate and hyaluronic acid. It is now undergoing biological testing as described below.

It is anticipated that once injected into the blood stream, that there would be enough heparan sulfate and hyaluronic acid to fill out the syndecan scaffold. In certain embodiments, the glycocalyx composition is injected into blood stream for therapeutic use.

Another exemplary nanoliposomal formulation (B) is tabulated below.

Pegylated Liposomes

| Lipids | Cat # | MW | Mole % |
|---|---|---|---|
| DSPC | 850365 | 790.145 | 49 |
| cholesterol | 700000 | 386.654 | 30 |
| DSPE | 850715 | 748.065 | 15 |

-continued

| Lipids | Cat # | MW | Mole % |
|---|---|---|---|
| DSPE-PEG2000 | 880120 | 2805.497 | 5 |
| Aurora-PLC | 550002 | 550 | 1 |

Non Pegylated Liposomes:

| Lipids | Cat # | MW | Mole % |
|---|---|---|---|
| DSPC | 850365 | 790.145 | 54 |
| cholesterol | 700000 | 386.654 | 30 |
| DSPE | 850715 | 748.065 | 15 |
| Aurora-PLC | 550002 | 550 | 1 |

It is expected that a number of variations and improvements will be developed based on the basic restorative glycocalyx composition described herein, and may include one or more of the following options.

Variations on the Targeting Motif

A monoclonal antibody (Mab) to CD31 can be utilized in the restorative glycocalyx composition to target the composition to global endothelium, as there is a systemic endothelial dysfunction in septic or ischemic acute kidney injury (AKI). This is achieved by coupling of a fragment of Mab (reduced thiol groups Fab fragment) joined via surface linkage to liposomes, as detailed previously (38-40). Although this strategy is broadly used in anti-cancer formulations, it has not previously been applied to targeting global endothelium. Targeting to specific receptors may increase receptor-mediated endocytosis of liposomes, whereas the goal of the present nanoliposomes and treatments is to increase their fusion with the plasma membrane. Initial testing will provide guidance on whether this targeting serves to increase fusion of the restorative glycocalyx nanoliposome composition to the plasma membrane.

Fusogenic Liposomes

In additional embodiments, compositions incorporating fusogenic liposomes will be developed to improve incorporation in the plasma membrane. These formulations have been extensively used (for instance, 41, 42). The technology to manufacture fusogenic liposomes consists of incorporating special lipids making liposomes more fluid and capable to destabilize the plasma membrane (43, 44, and CA2252055 A1, 16 Oct. 1997).

Sulodexide-Fortified Liposomes—Examples of Additional Active Agents in the Glycocalyx Composition.

In further embodiments, the heparan sulfate (HS) moiety in liposomal nanocarriers will be enhanced by admixture of a fast-moving fraction of heparin—Sulodexide (e.g. an additional active agent to the composition), to slow down the degradation of liposomal preassembled glycocalyx structures (36,37). It is expected that this optional variation in the composition will improve stability of the restorative composition.

Poly-(Ethylene Glycol) (PEG) Modified-Liposomes

In further embodiments, poly-(ethylene glycol) (PEG)-liposomes ("stealth") will be generated to a) prolong the half-life of the restorative glycocalyx compositions in the circulation and on the cell surface by enhancing resistance to sheddases and also to b) evade immune system, which is especially important for in vivo use and long-term functional monitoring. In vivo, liposomes are rapidly taken-up by mononuclear phagocyte system (45,46). PEGylation is most frequently achieved by linking PEG to the liposomal membrane via a lipid linker, as distearoylphosphatidylethanolamine, as well as simply by physical absorption onto the surface of liposomes. Advantages of PEG are many and include biocompatibility, solubility in water, lack of toxicity, low immunogenicity and eventual excretion. PEGylation decelerates the clearance of liposomes by phagocytes through reduced opsonization. Importantly, with respect to the present restorative glycocalyx compositions, it is possible to reduce phagocytic uptake of liposomes by pretreating the patient with "ghost" liposomes to saturate phagocytic uptake capacity (46)—this strategy will be utilized in in vivo experiments in various model animals.

Gold-Labeled Liposomes

To facilitate their recognition by electron microscopy imaging, the restorative glycocalyx nanoliposome compositions may be gold-labeled. A simple technique of preparing liposomes together with colloidal gold can be followed (gold chloride/citrate in the aqueous phase) and detection in endothelial cells with labeled liposomes has been reported (47).

It is expected that the restorative glycocalyx nanoliposome compositions described herein (e.g. dandelion therapy) will have a broad application in cardiovascular diseases and diabetes, as well as inflammatory and other conditions.

EXAMPLES

Example 1—In Vitro Testing of Liposomal Carriers of EG Components—AFM and Fluorescence Microscopy for Detection of EG Electron microscopy studies of renal microvascular endothelial cells (RMVEC) treated with these liposomes demonstrated their adhesion to RMVEC surface, as depicted in representative images in FIG. 5. Notably, when attaching to intact cells (109 liposomes/ml) we found 14 liposomes along 94,145 nm of plasma lemmal length, but after degradation of glycocalyx with heparanase III, 34 liposomes were found attached along 44,011 nm of plasma lemma, thus demonstrating preferential attachment to the plasma membranes with degraded EG.

Figure 6:
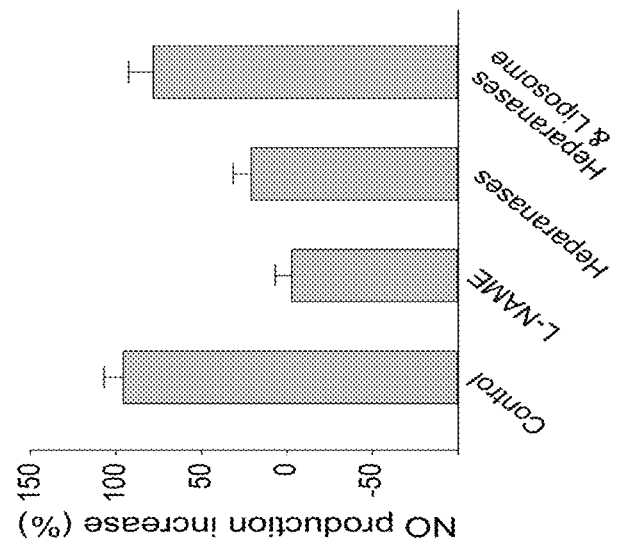
FIG. 6 is a graph showing the effect of degradation of endothelial glycocalyx on NO production in the presence and absence of restorative glycocalyx nanoliposomes. Prior to the assay, endothelial monolayers were either untreated (control group) or treated with the following reagents: 25 mU/ml heparanases I and III, 100 μM L-NAME, or heparanases followed by restorative glycocalyx nanoliposomes ($12.9 \times 10^8$/ml). The cells were then loaded with DAF-FM at a concentration of 5 μM. The endothelial monolayers were exposed to a shear stress of 10 dynes/cm2 for 20 minutes. Images were taken prior to and after shear exposure. The DAF fluorescence of each image was quantified with NIH ImageJ. The fluorescence intensity post shear stimulation was normalized by the intensity prior to shear exposure. The data was expressed as the % increase (or decrease) of NO production. Experiments were repeated at least 3 times. The error bars are standard deviation.

The effect of heparanase III-induced degradation of EG in cultured endothelial cells was examined. Shear flow-induced activation of nitric oxide (NO) production was detected using fluorescence microscopy of DAF-FM. As shown in FIG. 6, L-NAME has completely abolished shear-induced NO production. Remarkably, the similar effect was observed after degradation of EG. Treatment of endothelial cells with nanoliposomes resulted in a significant restoration of shear-induced NO production.

Example 2—Ex Vivo Testing of Liposomal Carriers of EG Components

Figure 7:
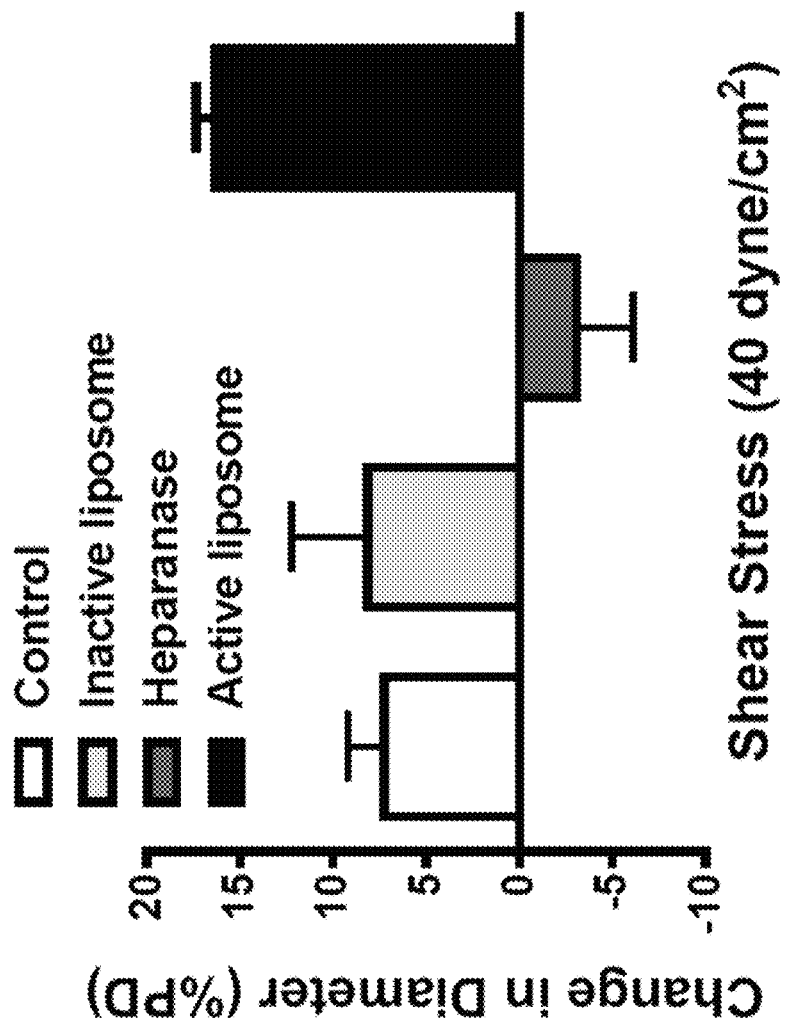
FIG. 7 is a graph reflecting isolated perfused resistance arteries (ca 100 μm in diameter)—flow-induced vasodilation. Heparanase III treatment abolished flow-induced dilation, whereas treatment with restorative glycocalyx nanoliposomes ($12.9 \times 10^8$/ml) resulted in significant improvement of vasodilatory responses to flow.

Flow-induced vasorelaxation is a time-tested technique to interrogate mechanotransduction, one of the functions of EG. In preliminary studies, we next examined the effect of nanoliposomes on the shear flow-induced vasodilation in perfused mesenteric vessels, a classical object for this type of studies. The 1st-order mesenteric arteries were used. the average diameter and length of isolated arteries were about 250 micrometers and 10 mm (n=4). 80 mmHg intravascular pressure was given. Flow equivalent to 20 and 40 dyne/cm$^2$ shear stress was applied to the vessels for 10 minutes in control and after administration of active liposomal particles. As shown in FIG. 7, treatment with heparanase completely abolished flow-induced vasodilation. Inactive liposomes showed a modest restoration of vasodilation, whereas the active nanoliposomal preparation more than doubled the effect of control preparation.

Thus, preliminary testing of the restorative glycocalyx nanoliposome compositions described herein provide support to the therapeutic goals, including that the glycocalyx nanoliposome composition improves mechanosensing resulting in NO production and vasodilation, probably, due to improved EG integrity after its heparanase-induced degradation (which serves as a model of damaged or diseased EG in a patient).

Tables 1-2 listed below include optional proteoglycan core proteins, compositions of the disaccharides of various glycosaminoglycan chains, which may be useful options in the present compositions. Additionally, Table 3 shows exemplary molecules dependent on interaction with the endothelial glycocalyx for proper functioning.

TABLE 1

Characteristics of proteoglycan core proteins in the vascular endothelial glycocalyx

| Core protein group | Core protein size (kDa) | Number of subtypes | Number of GAG-chains linked | Type of GAG-chains linked | Structural relation to cell membrane |
|---|---|---|---|---|---|
| Syndecan | 19-35 | 4 | 5 | HS/CS | Membrane-spanning |
| Glypican | 57-69 | 6 | 3 | HS/CS | GPI-anchor |

GAG Glycosaminoglycan,
HS heparan sulfate,
CS chondroitin sulfate,
DS dermatan sulfate,
KS keratan sulfate,
GPI glycosylphosphatidylinositol In certain embodiments, the proteoglycan can be a perlecan, versican, decorin, blglycan, or mimecan, with no preference for any one sub-type.

In certain preferred embodiments, the proteoglycan can be syndecan 1 or 4, which are expressed and induced by inflammation, while other syndecan subtypes are less expressed on endothelial tissue.

In certain embodiments, the proteoglycan can be a glypican—with no preference for any one type of glypican.

TABLE 3

Molecules dependent on interaction with the endothelial glycocalyx for proper functioning

| Interacting molecule | Primary function in vasculature |
|---|---|
| Antithrombin III | Potent inactivator of pro-coagulant proteases such as thrombin, factor Xa and factor IXa; activity enhanced by heparin or heparan sulfate |
| Heparin cofactor II | Inactivator of the procoagulant protease thrombin; activated by dermatan sulfate in the endothelial glycocalyx |
| TFPI | Anticoagulant protein blocking activated factor VII and X |
| LPL | Enzyme involved in breakdown of low density lipoproteins |
| LDL | Transports cholesterol and triglycerides through the circulation |
| VEGF | Potent stimulator of angiogenesis, production of which is triggered by hypoxia |
| TGFβ1/2 | Growth factor known to mediate in a lot of signaling pathways, including smooth muscle cell differentiation and vascular tone and reactivity |
| FGF(r) | Growth factor (receptor) involved in endothelial cell proliferation and angiogenesis |
| Ec-SOD | Extracellular quencher of reactive oxygen species |
| IL 2, 3, 4, 5, 7, 8, 12, RANTES | Chemotaxis of leukocytes to the subendothelium; involved in arrest and diapedesis |

TFPI Tissue factor pathway inhibitor,
LPL lipoprotein lipase,
LDL low density lipoprotein,
VEGF vascular endothelial growth factor,
TGFβ1/2 transforming growth factor β1 or β2,
FGF(r) fibroblast growth factor (receptor),
ec-SOD extracellular superoxide dismutase,
IL interleukin,
RANTES Regulated on Activation,
Normal T Expressed and Secreted-also known as chemokine CCL5

Tables 1-3 from: Reitsma, Sietze et al. "The Endothelial Glycocalyx: Composition, Functions, and Visualization." *Pflugers Archiv* 454.3 (2007): 345-359. *PMC*. Web. 23 Aug. 2017.

Example 3—In Vitro Study of Preassembled Glycocalyx Liposomal Nanocarriers

Figure 8:
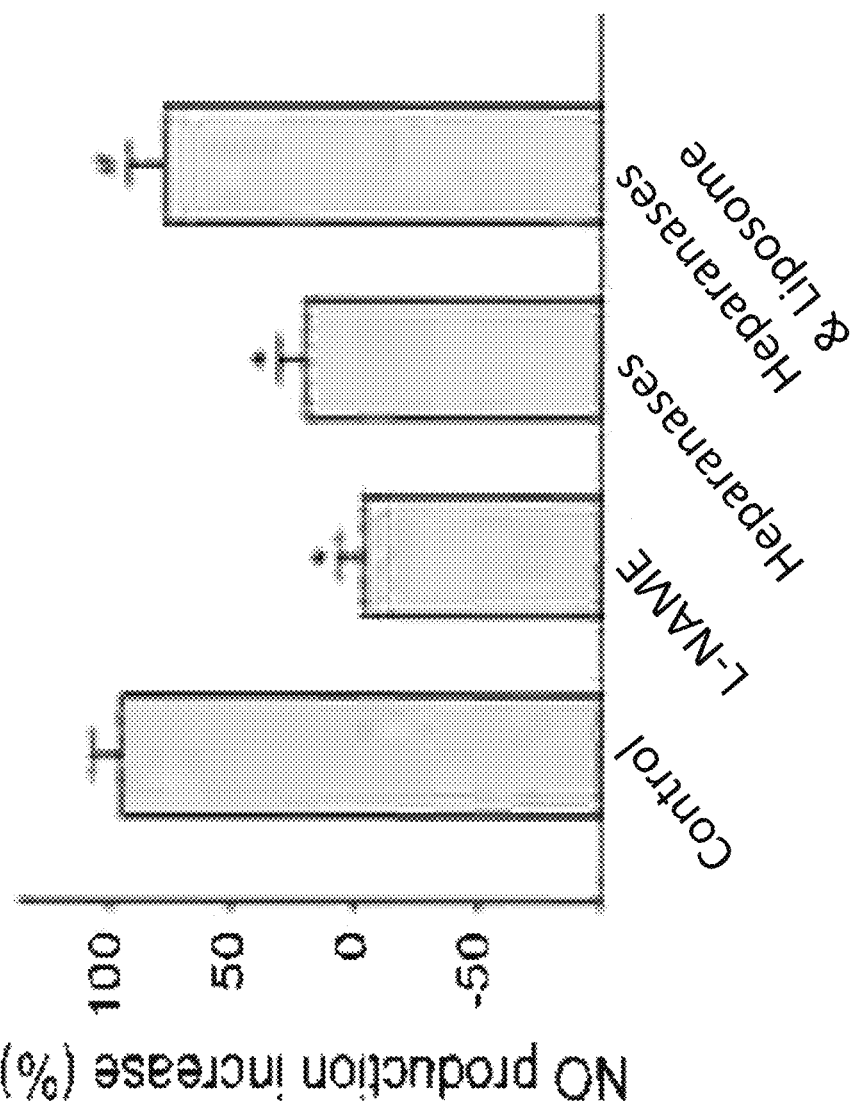
FIG. 8 is a bar graph showing NO production by endothelial cells in vitro.

The effect of heparanase III-induced degradation of EG in cultured endothelial cells was examined. Shear flow-induced activation of nitric oxide (NO) production was detected using fluorescence microscopy of OAF-FM. As shown in FIG. 8, L-NAME completely abolished shear-induced NO production. A similar effect was observed after degradation

TABLE 2

Composition of the disaccharides of various glycosaminoglycan chains

| | Heparan sulfate | Chondroitin sulfate | Dermatan sulfate[a] | Hyaluronan | Keratan sulfate |
|---|---|---|---|---|---|
| Uronic acid | GlcA(2S) IdoA(2S) | GlcA | GlcA IdoA(2S) | GlcA | Gal(6S) |
| Disaccharide link | 1β4 | 1β3 | 1β3 | 1β3 | 1β4 |
| Hexosamine | GlcNAc(NS)(3S)(6S) | GalNAc4S[a] GalNAc6S[a] | GalNAc(4S)(6S) | GlcNAc | GlcNAc(6S) |
| Polymerization link | 1β4 | 1β4 | 1β4 | 1β4 | 1β3 |

Note the various possibilities of sulfation in heparan sulfate. These may coincide (e.g., in heparan sulfate the hexosamine GlcNS3S). A rare but possible hexosamine in heparan sulfate is the N-unsubstituted glucosamine (GlcNH$_3^+$), which has been left out of the table for convenient reading. Also note the presence of IdoA in dermatan sulfate, in contrast to the other chondroitin sulfates, making it more alike to heparan sulfate.
GlcA Glucuronic acid, IdoA iduronic acid, Gal galacturonic acid, GlcNAc N-acetyl-glucosamine, GalNAc N-acetyl-galactosamine, 2S 2-O-sulfated, 3S 3-O-sulfated, 4S 4-O-sulfated, 6S 6-O-sulfated, NS N-sulfated
[a]There are three types of chondroitin sulfate. Type A only has 4-O-sulfated N-acetyl-galactosamines, type B is known as dermatan sulfate and type C only has 6-O-sulfated N-acetyl-galactosamines.

of EG. Treatment of endothelial cells with nanoliposomes resulted in a significant restoration of shear-induced NO production.

Endothelial cells loaded with DAF-FM diacetate were stimulated with stretch applied by AFM cantilever. Results presented in FIG. 9 demonstrate that, while stretching intact cells resulted in NO production, this effect was absent in cells pretreated with heparanase Ill. Treatment with nanoliposomes of heparanase Ill-pretreated cells restored NO production in response to stretch.

The effect of degradation of endothelial glycocalyx on NO production in the presence and absence of nanoliposomes was studied. FIG. 1. Prior to the assay, endothelial monolayers were either untreated (control group) or treated with the following reagents: 25 mU/ml heparanases land Ill, 100 uM L-NAME, or heparanases followed by nanoliposomes (12.9×108/ml). The cells were then loaded with OAF-FM at a concentration of 5 PM. The endothelial monolayers were exposed to a shear stress of 10 dynes/cm2 for 20 minutes. Images were taken prior to and after shear exposure. The OAF fluorescence of each image was quantified with NIH ImageJ. The fluorescence intensity post shear stimulation was normalized by the intensity prior to shear exposure. The data was expressed as the % increase (or decrease) of NO production. Experiments were repeated at least 3 times. The error bars are standard deviation.

Figure 9:
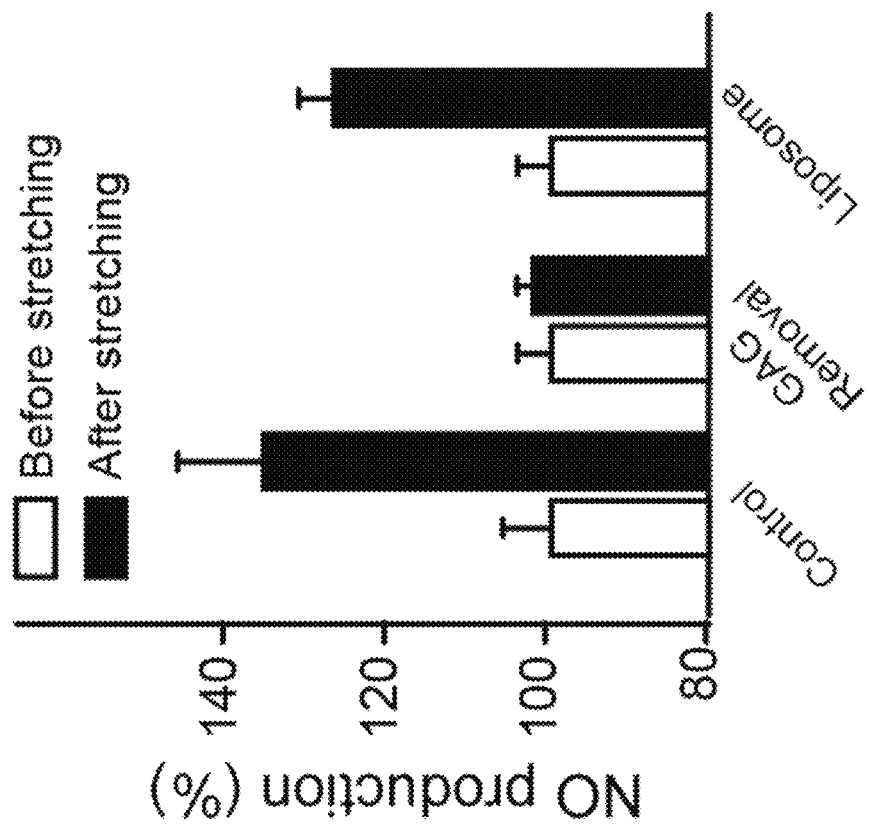
FIG. 9 is a bar graph showing endothelial cell NO production before and after stretching.

The effect of liposome with the AFM assay was tested. FIG. 9. The cells were either untreated (control), or treated with the various indicated reagents prior to stretching. GAG was removed using heparanase and hyaluronidase.

Figure 3:
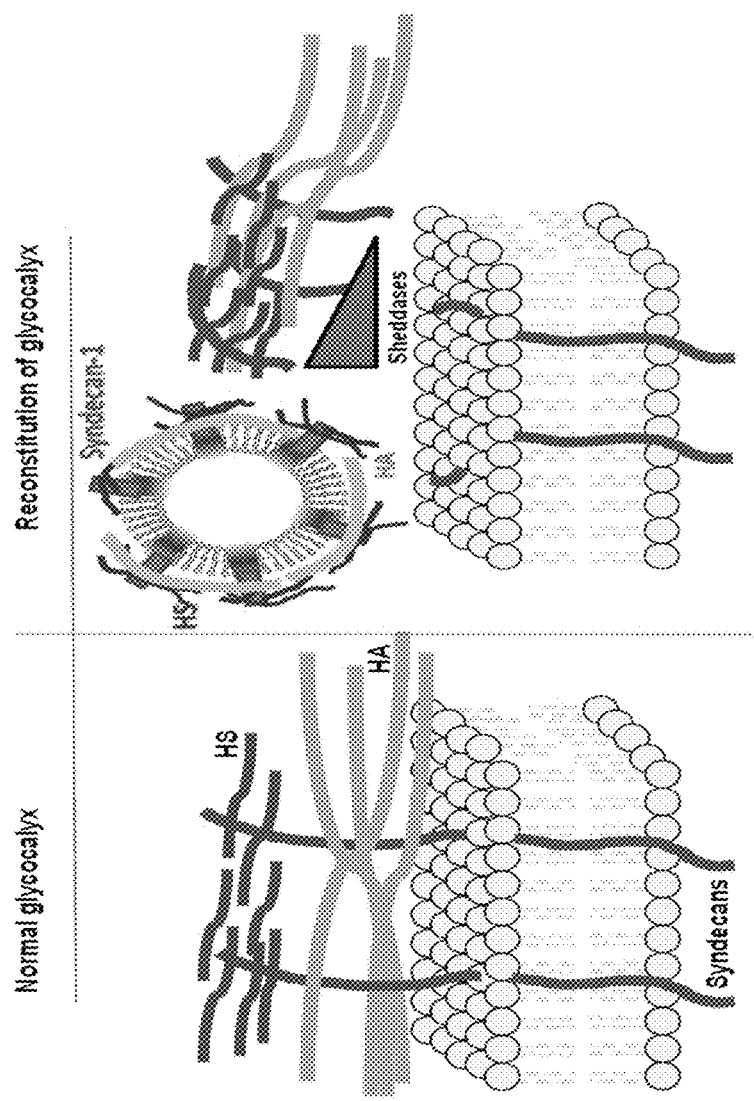
FIG. 3 is a diagram showing the proposed mode of regeneration of glycocalyx (left side) after its degradation by the activated sheddases (right side). Abbr: HS—heparin sulfate; HA-hyaluronic acid. The lipid bilayers at the bottom represent any plasma membrane.
Figure 4:
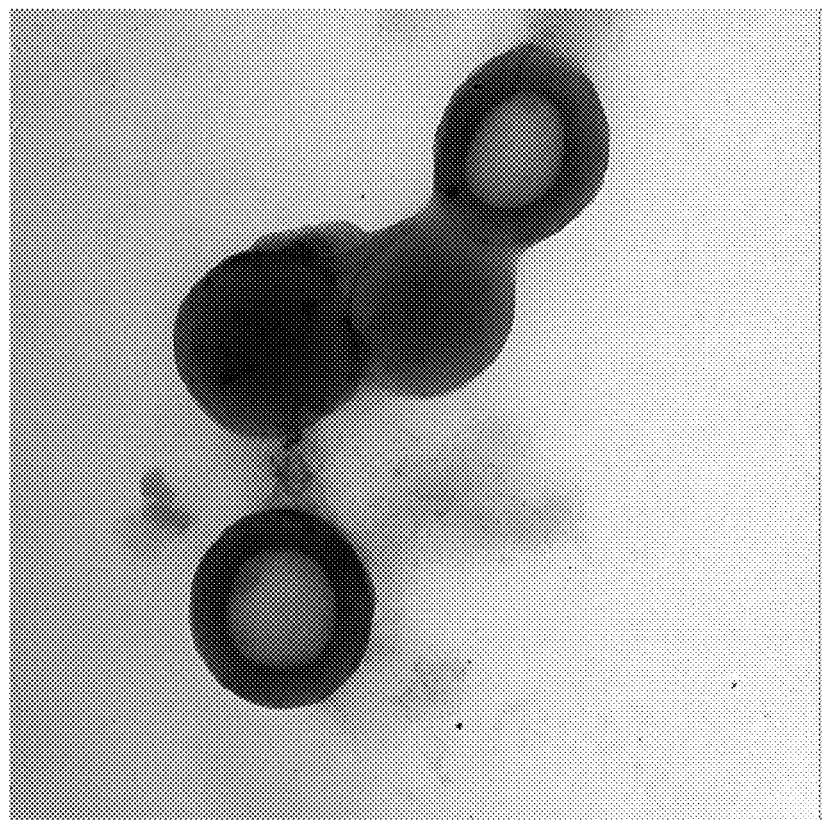
FIG. 4 shows images of electron microscopy of nanoliposomes with preassembled EG (e.g. restorative glycocalyx composition) ($12.9 \times 10^7 - 10^8$ per ml). Negative staining was performed as follows. Five μl of suspension were applied to a 400 mesh, formvar-carbon coated copper grid. After 1 minute, the excess solution was wicked away with filter paper and 4 successive drops of 1.5% uranyl acetate (aqueous) were added and wicked. After removal of the 4th drop of stain, the grid was allowed to air-dry. All samples were viewed in a JEOL JSM 1400 TEM operating at 100 Kv. Images were captured on a Veleta 2K×2K CCD camera (EMSIS GmbH).

EG was measured in cultured endothelial cells stripped of their glycocalyx using heparanases or LPS application and treated with liposomal carriers of preassembled EG. Using AFM and nanoindentation of endothelial cells (FIG. 3) similar results were obtained—liposomal treatment improved EG thickness.

Figure 10:
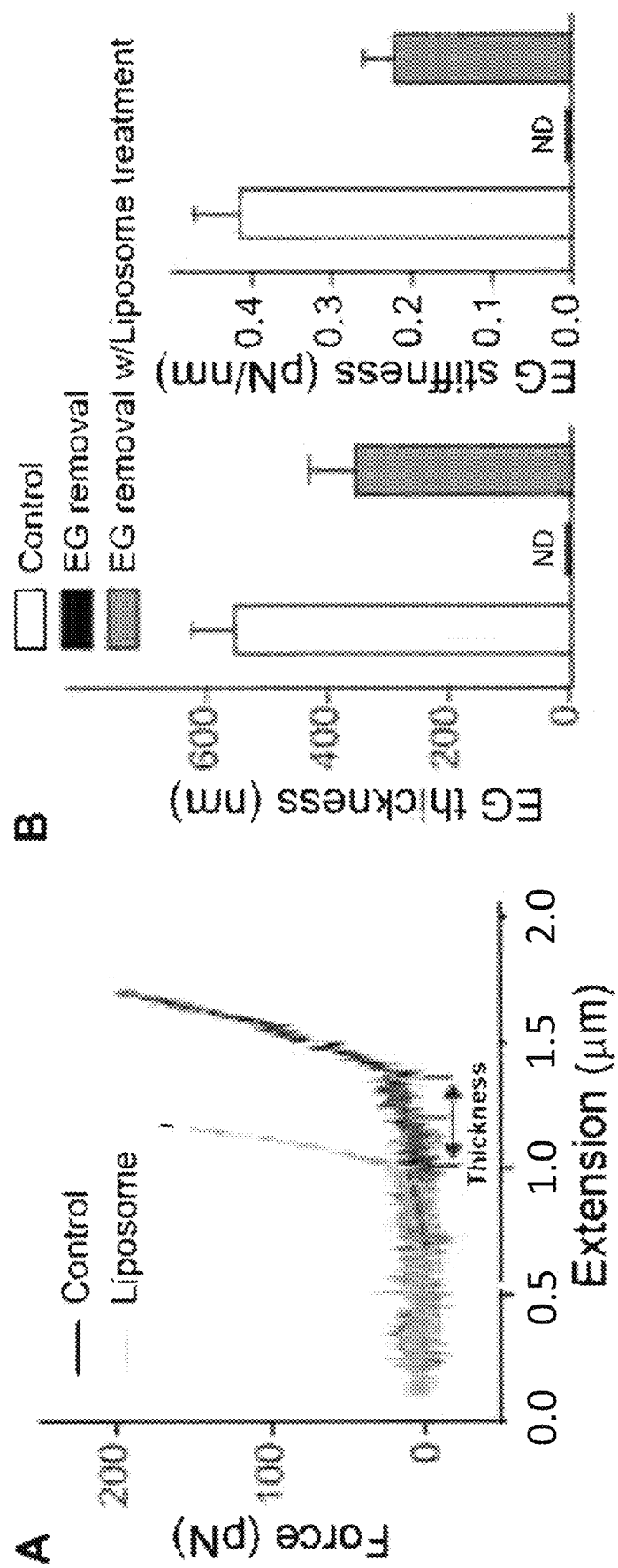
FIG. 10 shows results of atomic force microscopy: graphs of (A) representative actual force-extension curves and (B) EG thickness in control, after EG enzymatic removal in the presence and absence of liposomes with preassembled glycocalyx.

Nanoindentation of endothelial glycocalyx was shown using atomic force microscopy. FIG. 10(A) shows representative actual force-extension curves and FIG. 10(B) shows a summary on EG thickness in control, after EG enzymatic removal in the presence and absence of liposomes with preassembled glycocalyx.

Example 4—Ex Vivo and In Vivo Studies of Glycocalyx in a Mouse Sepsis Model

Figure 11:
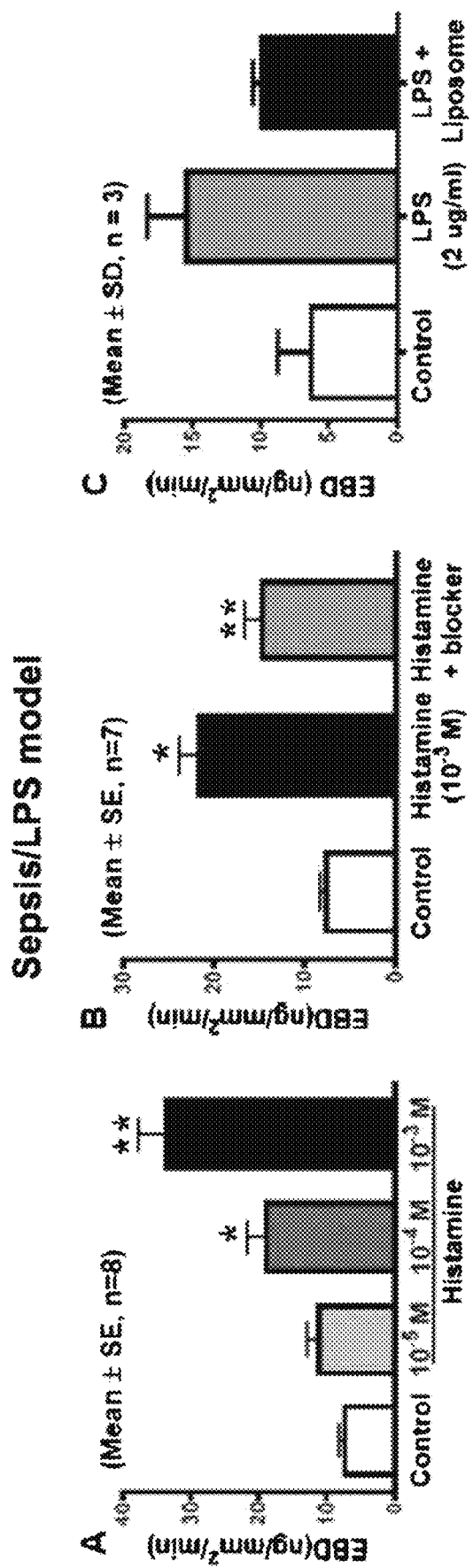
FIG. 11 shows graphs of changes in mouse mesenteric venule permeability in controls compared to (A) histamine, (B) histamine and histamine+blocker, and (C) LPS and LPS+liposome.

Changes in permeability of mouse mesenteric venules are shown in FIG. 11. EBO is normalized by the surface area of vessels and a 60 min incubation time.

EM imaging of LPS injected mouse kidney showed severe damage to endothelial glycocalyx. In contrast, perfusion of liposomal carriers of the preassembled glycocalyx was associated with a remarkable improvement of endothelial glycocalyx. On the surface of visibly damaged peritubular and glomerular capillary endothelial cells liposomes were readily discernible as tethered, implanted and fused forms (FIG. 12), thus confirming the prediction of incorporation and fusion of liposomes with the cell surface.

Figure 12:
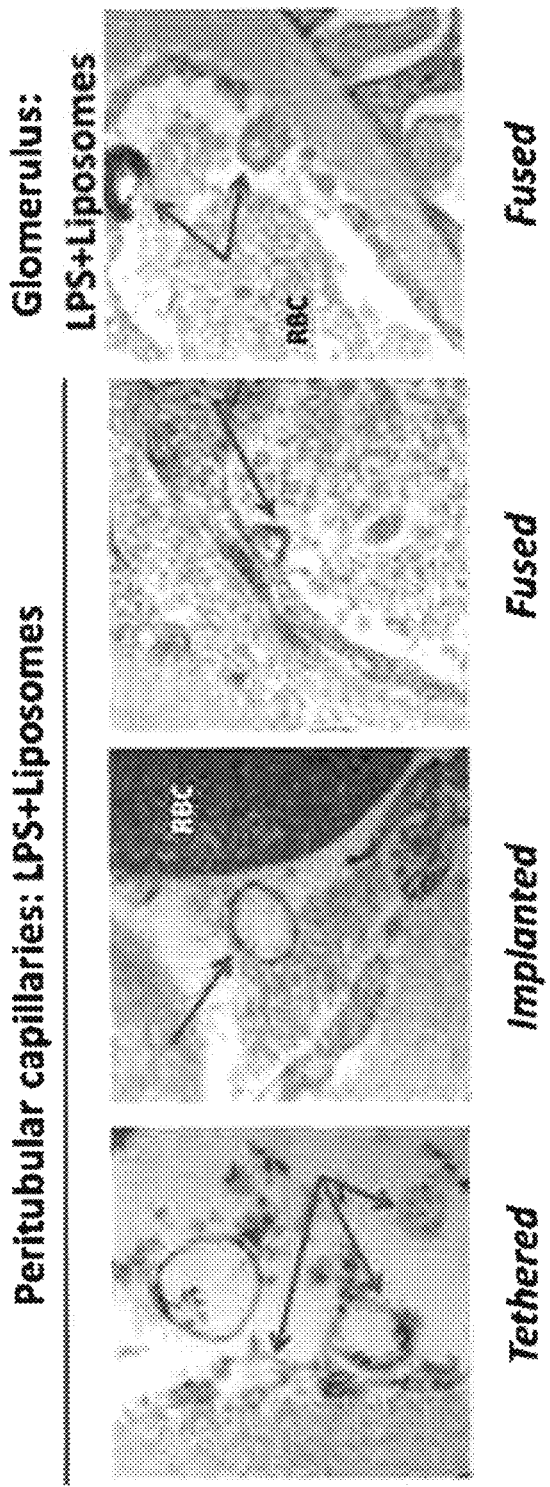
FIG. 12 shows a TEM of the mouse kidney after LPS, which was then infused with the liposomal carriers of the preassembled glycocalyx. Note that some liposomes are free in the circulation, others are tethered to the endothelial cell surface, yet others are implanted or fused (red arrows). Liposomes were found also attached to the surface of RBC (not shown).

A TEM of mouse kidney after LPS infused with the liposomal carriers of the preassembled glycocalyx showed that some liposomes are free in the circulation, others are tethered to the endothelial cell surface, yet others are implanted or fused (FIG. 12). Liposomes were found also attached to the surface of RBC (not shown).

Figure 13:
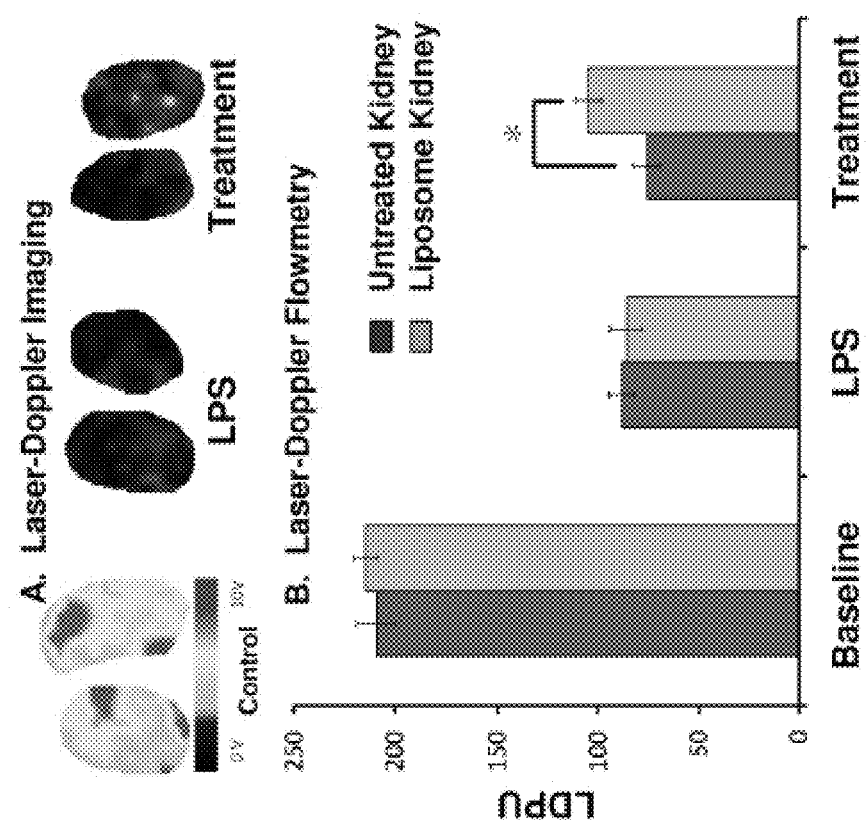
FIG. 13 shows images and bar graphs of LPS injection and microcirculatory parameters of liposome-perfused and non-perfused kidney. Laser-Doppler imaging (A) and flowmetry (B) were performed prior to LPS injection, 30 min after the injection, but prior to initiation of liposome perfusion, and 30 min after perfusion of liposomal carriers of the preassembled glycocalyx (10 ul/min at concentration of $12.9 \times 10^9$ liposomes/ml). LPS was injected i/p at 5 mg/kg. In (A) the color scale is shown. In (B) asterisk denotes p<0.05 between perfused and non-perfused sides.

As shown in FIG. 13, studies of laser-Doppler images and flowmetry prior to, after LPS, and following infusion of nanoliposomes with the preassembled glycocalyx reveal an improvement of renal microcirculation. These findings are consistent with the ability of liposomal carriers of the preassembled glycocalyx to restore endothelial glycocalyx and improve renal microcirculation.

Example 5—In Vitro and In Vivo Studies in a Mouse Model of Diabetes with Metabolic Syndrome AFM nanoindentation studies of cultured renal microvascular endothelial cells isolated from db/db mice were performed.

Figure 14:
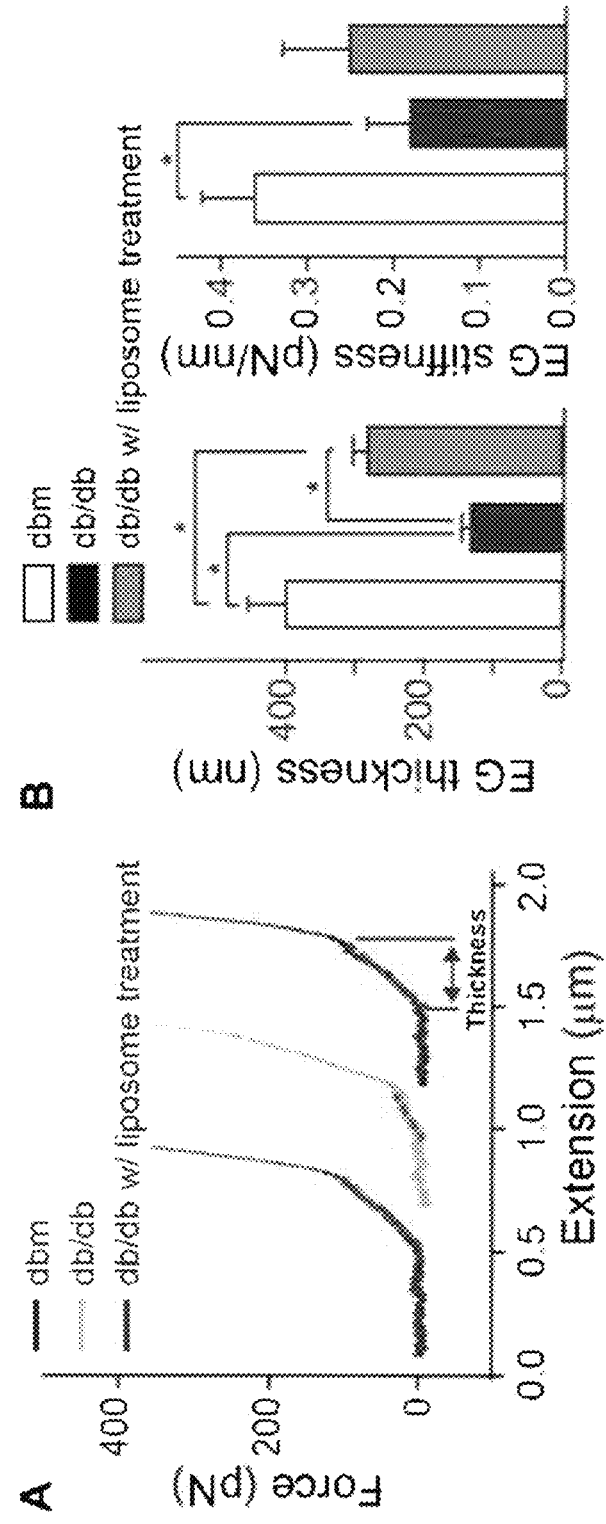
FIG. 14—Nanoindentation of EG of DB/DB RMVEC using AFM: (A) representative force-extension curves of nanoindentation experiments, and (B) summary on EG thickness and stiffness in Dbm control, Db/db and Db/db after treatment with liposomal nanocarriers of preassembled glycocalyx.

Using AFM, nanoindentation of EG of DB/DB RMVEC was observed. FIG. 14(A) shows representative force-extension curves of nanoindentation experiments, and FIG. 14(B) shows a summary on EG thickness and stiffness in Dbm control, Db/db and Db/db after treatment with preassembled glycocalyx. The observed vasodilation was due to the increased production of NO (improved mechanosensing).

Figure 15:
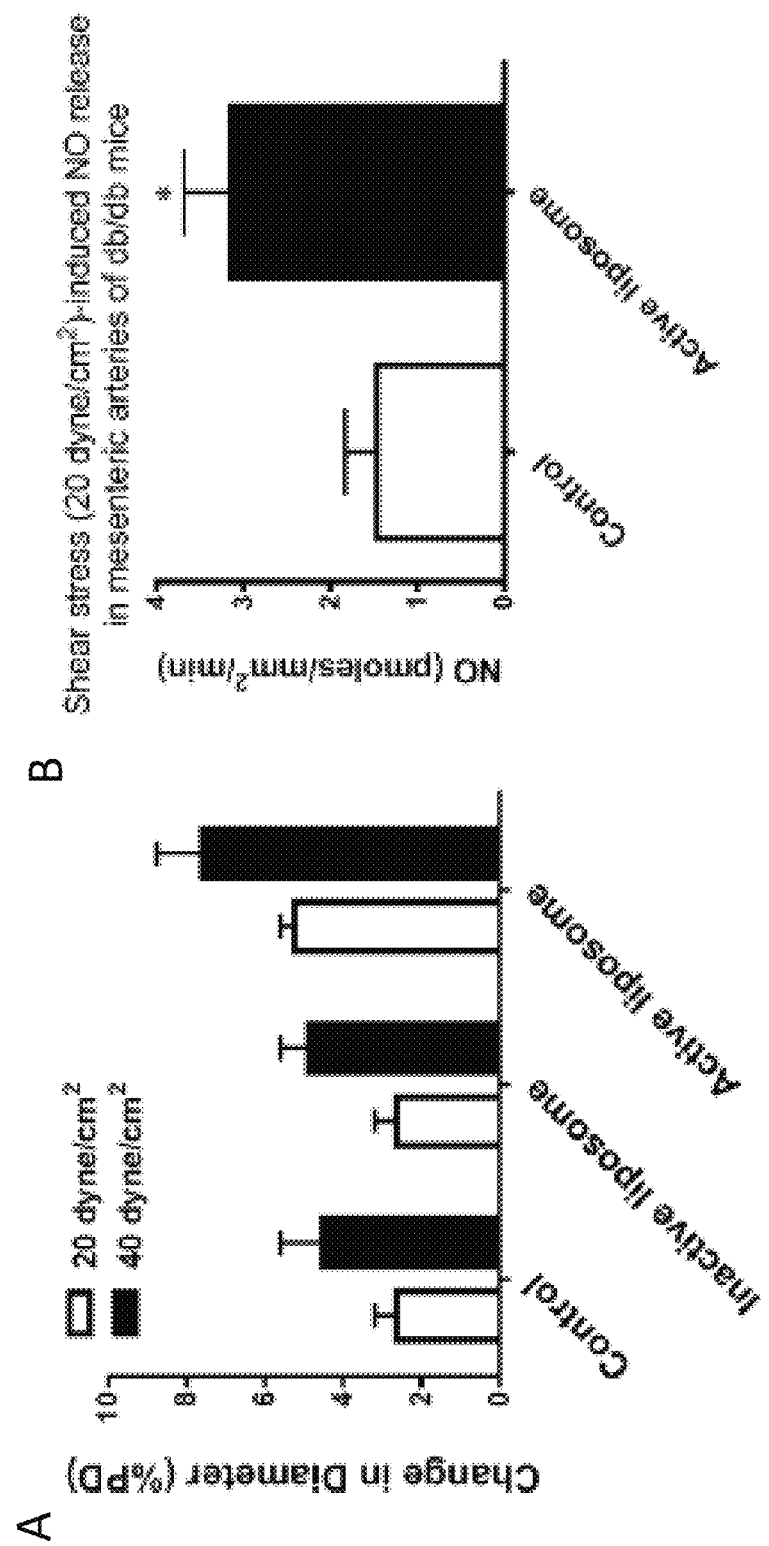
FIG. 15 (A) is a graph showing shear flow-induced vasodilation in vessels treated with liposomal nanocarriers of the preassembled glycocalyx (active) as opposed to "empty" (inactive) liposomes. HPLC detection of nitric oxide in the effluent (B) confirmed that the observed vasodilation was due to the increased production of NO (improved mechanosensing).

Isolated mesenteric arteries from 12-13 week-old male db/db mice were perfused. As shown in FIG. 15, shear flow-induced vasodilation (A) was significantly improved in expeditious fashion in vessels treated with liposomal nanocarriers of the preassembled glycocalyx (active) as opposed to "empty" (inactive) liposomes. HPLC detection of nitric oxide in the effluent (B) confirmed that the observed vasodilation was due to the increased production of NO (improved mechanosensing).

Treatment of perfused mesenteric arteries with liposomal carriers of the preassembled glycocalyx improves shear flow-induced vasodllation and NO production, Indicative of improvement In mechanosensing of db/db arteries. FIGS. 15(A) and (B).

Figure 16:
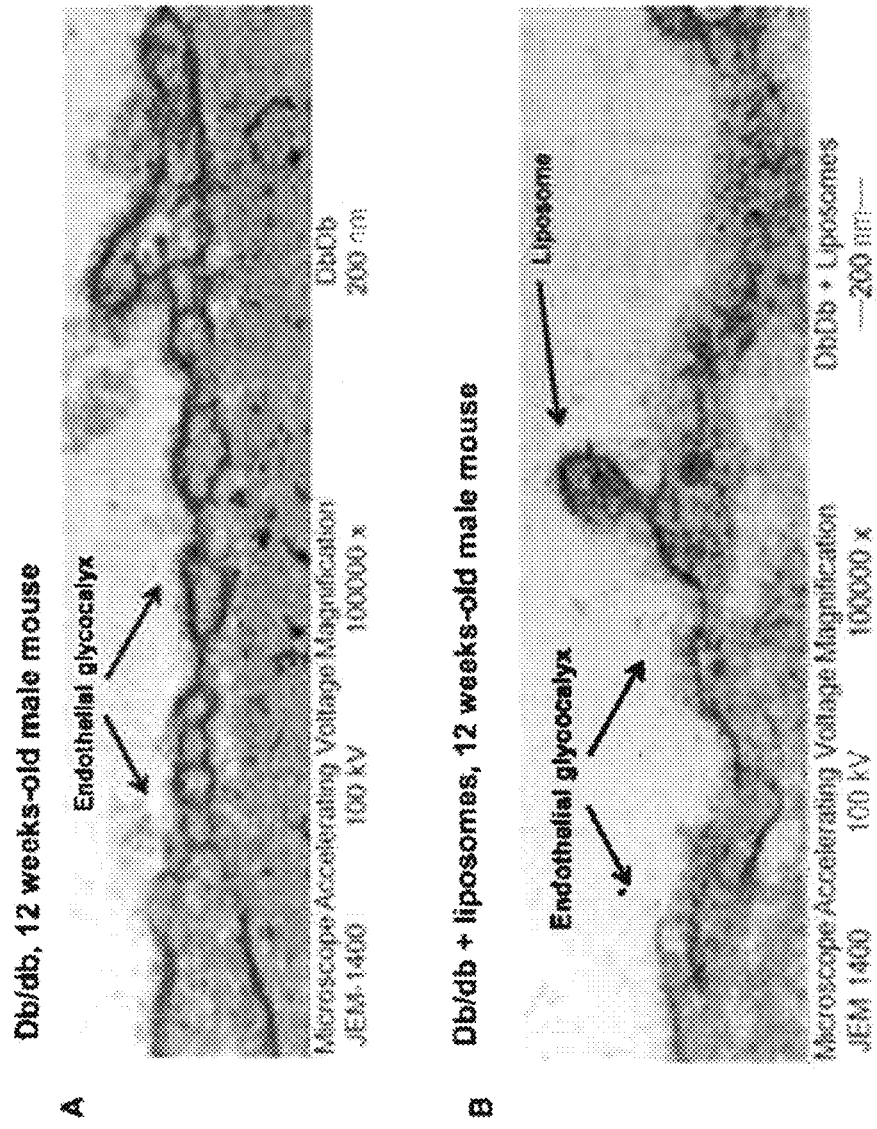
FIG. 16 shows representative images of renal microvascular endothelium in a db/db mouse before (A) and (B) after a single infusion of liposomal nanocarriers of preassembled glycocalyx. Note that the glycocalyx is severely damaged in both cases. Position of a liposome is indicated by the arrow.
Figure 17:
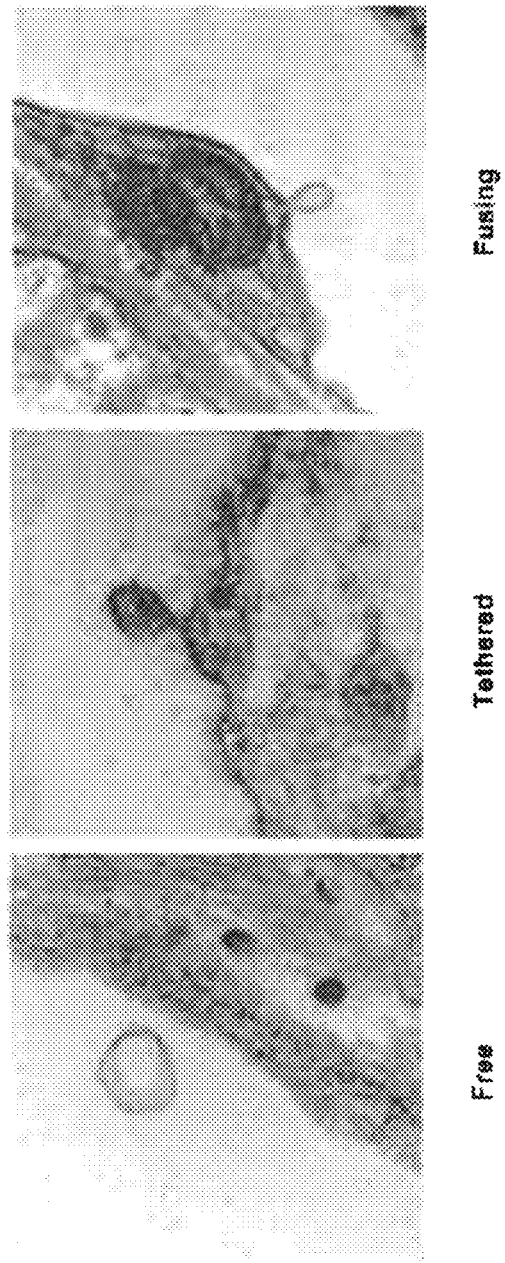
FIG. 17 was EM images of nanolipomes free in circulation, tethered to the luminal plasma membrane of endothelial cells, and fusing with the luminal plasma membrane of endothelial cells.

The renal artery of db/db mice were infused with liposomal nanocarriers of the preassembled glycocalyx. The contralateral kidney served as control. EM studies revealed a severe damage to the endothelial glycocalyx (FIG. 16). Nanoliposomes were observed in the treated side as free in the circulation, tethered to the luminal plasma membrane of endothelial cells and fusing with it (FIG. 17).

Figure 18:
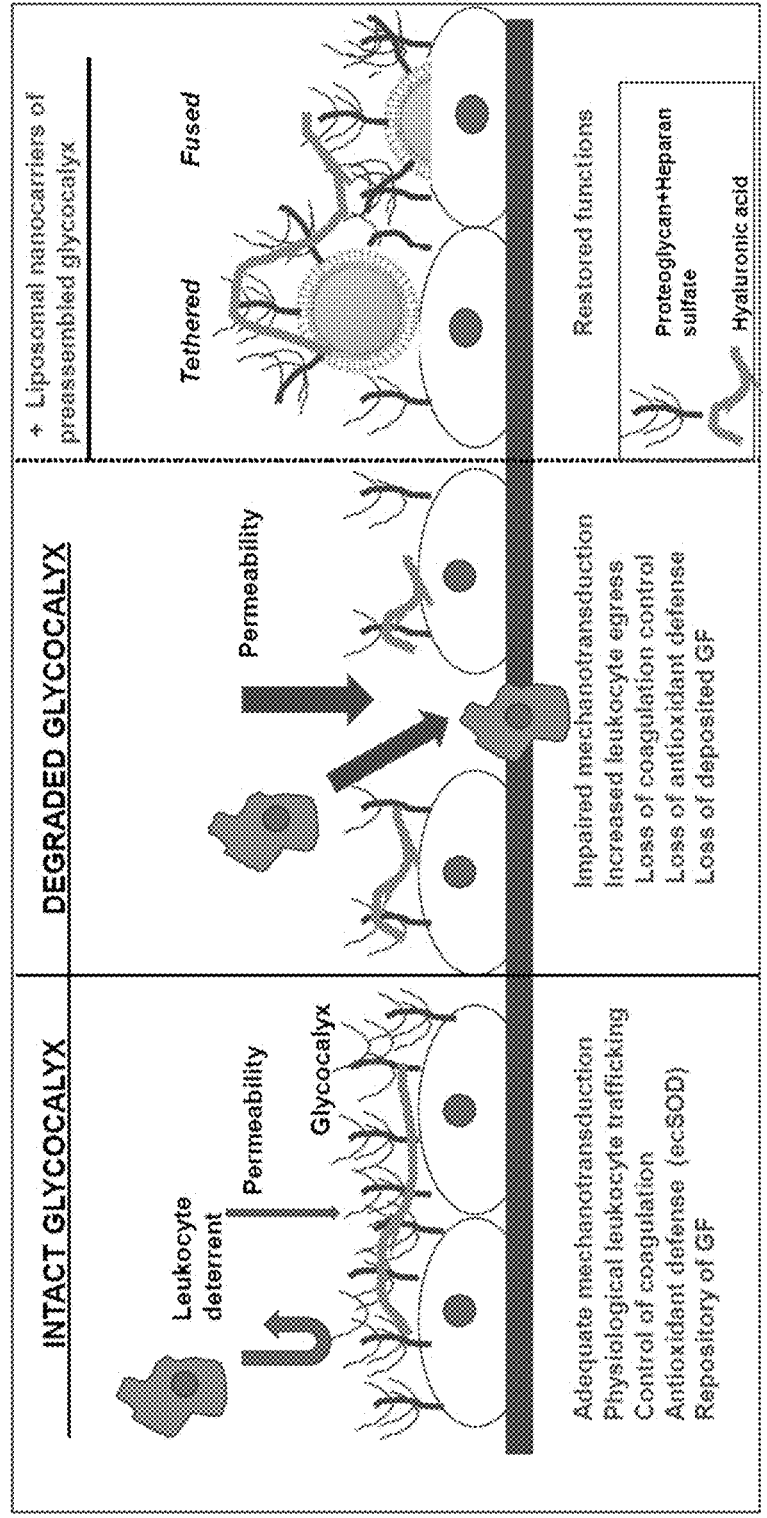
FIG. 18 is a schematic depiction of damaged endothelial glycocalyx, its consequences, and its restoration using liposomal nanocarriers of preassembled glycocalyx.

These studies support the main tenet of the proposal that liposomal nanocarriers of the preassembled glycocalyx attach and fuse with the plasma membrane, may improve microcirculations under acute conditions like sepsis, but could require repeated infusions in chronic conditions, like diabetes with metabolic syndrome. These studies further support the notion that liposomal nanocarriers of the preassemble glycocalyx have the capacity to expeditiously fuse with endothelial cells and repair the damaged glycocalyx, as schematically depicted in FIG. 18.

Figure 19:
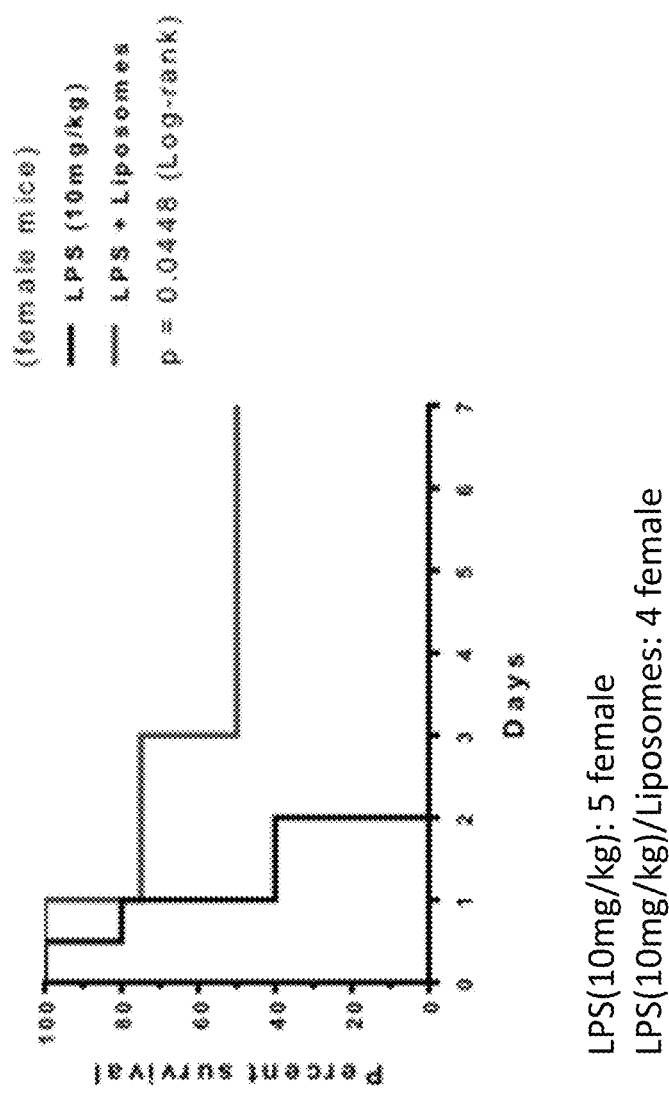
FIG. 19 is a graph showing data on survival of 5 female mice plotted against time and analyzed using log-rank statistical analysis.
Figure 20:
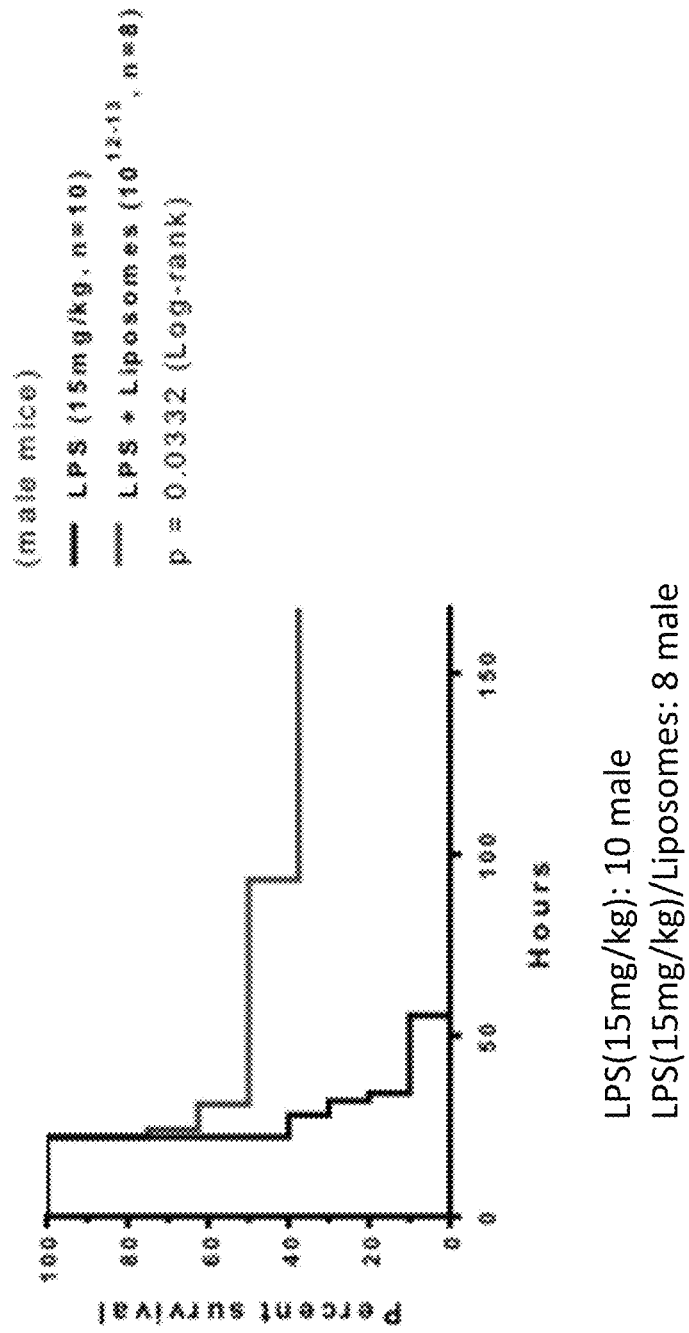
FIG. 20 is a graph showing data on survival of 10 male mice plotted against time and analyzed using log-rank statistical analysis.
Figure 21:
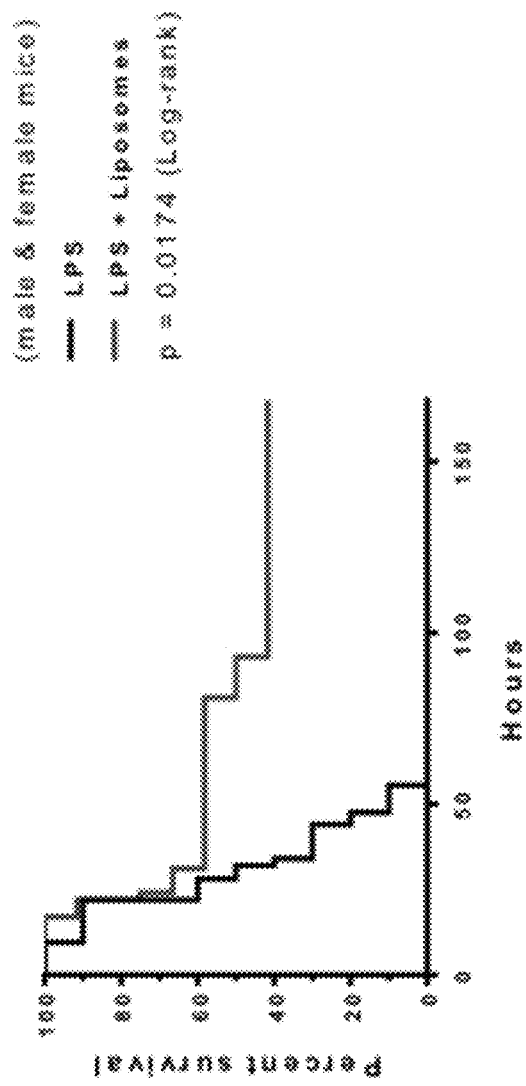
FIG. 21 is a graph showing data on survival of 5 female and 5 male mice plotted against time and analyzed using log-rank statistical analysis.

Example 6—Pre-Clinical Model on the Effect of Glycocalyx Liposomes in LPS-Induced Septic Shock in Mice 12-15 week-old mice were housed in cages equipped with video-cameras. Mice were injected IP with 10 mg/kg LPS. Liposomal nanocarriers of preassembled glycocalyx (1013 liposomes/ml; total volume of 200 ul per mouse—2nd generation of PEGylated liposomes) were injected IV into the tail vein within 1 h post-LPS injection, at the height of inflammatory response. The time of death was registered on video-recordings. Data on survival were plotted against time and analyzed using Log-rank statistical analysis. FIGS. 19-21. In mice injected with 10 mg/kg LPS, video-monitoring revealed that IV injection of liposomes (200 ul of 1013 liposomes) resulted in improved survival.

REFERENCES

1. Potter D, Jiang J, Damiano E. The recovery time course of the endothelial cell glycocalyx in vivo and its implications in vitro. Circ Res 2009; 104: 1318-25
2. Giantsos-Adams K, Koo A, Song S, Sakai J, Sankaran J et al. Heparan sulfate regrowth profiles under laminar shear flow following enzymatic degradation. Cell Mol Bioeng 2013; 6: 160-74
3. van den Berg B, Nieuwdrop M, Stroes E, Vink H. Glycocalyx and endothelial (dys)function: from mice to men. Pharmacol Rep 2006; 58 Suppl 75-80
4. Henry C, Duling B. Permeation of the luminal capillary glycocalyx is determined by hyaluronan. Am J Physiol 1999; 277: H508-14
5. Coccheri S, Mannello F. Develiopment and use of sulodexide in vascular diseases: implications for treatment. Drug Des Devel Ther 2014; 8: 49-65
6. Broekhuizen L, Lemkes B, Mooij H et al. Effect of sulodexide on endothelial glycocalyx and vascular permeability in patients with type 2 diabetes mellitus. Diabetologia 2010; 53: 2646-55
7. Giantsos-Adams K, Lopez-Quintero V, Kopeckova P, Kopecek J, Tarbell J, Dull R. Study of the herapeutic benefit of cationic copolymer administration to vascular endothelium under mechanical stress. Biomaterials 2011; 32: 288-294
8. Jacob M, Paul O, Mehringer L et al. Albumin augmentation improves condition of guinea pig hearts after 4 hours of cold ischemia. Transplantation 2009; 87: 956-965
9. Jacob M, Bruegger D, Rhm M, Welsch U, Conzen P, Becker B F. Contrasting effect of colloid and crystalloid resuscitation fluids on cardiac vascular permeability. Anesthesiology 2006; 104: 1223-1231
10. Ziolkowski A, Popp S, Freeman C, Parish C, Simeonovic C. Heparan sulfate and heparanase play key roles in mouse beta cell survival and autoimmune disease. J Clin Invest 2012; 122: 132-141
11. Song J W, Zullo J A, Liveris D, Dragovich M, Zhang X F, Goligorsky M S. Therapeutic Restoration of Endothelial Glycocalyx in Sepsis. J Pharmacol Exp Ther. 2017; 361(1):115-22.
12. Reitsma, Sietze et al. The Endothelial Glycocalyx: Composition, Functions, and Visualization. *Pflugers Archiv* 454.3 (2007): 345-359. *PMC*. Web. 23 Aug. 2017.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. A composition comprising: a proteoglycan, heparan sulfate, hyaluronic acid, and an antibody for targeting the composition to endothelial glycocalyx, wherein the composition is formulated as a nanoparticle, wherein the antibody comprises an anti-CD31, anti-CD117 (C-Kit), or anti-CD44 antibody.

2. The composition of claim 1, wherein the proteoglycan is selected from the group consisting of syndecan, glypican, perlecan, versican, decorin, biglycan, and mimecan.

3. The composition of claim 2, wherein the proteoglycan comprises syndecan-1, syndecan-2, syndecan-3 or syndecan-4, or mixtures thereof.

4. The composition of claim 3, wherein the syndecan is labeled with an electron microscopy detectable label.

5. The composition of claim 4, wherein the electron microscopy detectable label is gold.

6. The composition of claim 1, wherein the nanoparticle comprises micelles, liposomes, polymersomes, hydrogel particles or polymer particles.

7. The composition of claim 6, wherein the nanoparticle is a liposome and the liposome is optionally PEGylated.

8. The composition of claim 1, wherein the nanoparticle has a maximum linear dimension of 1000 nanometers.

9. The composition of claim 1, further comprising a drug or active agent.

10. The composition of claim 9, wherein the active agent heparan sulfate is substituted with sulodexide.

11. A method for restoring endothelial glycocalyx in at least one membrane in a patient in need thereof, comprising administering an effective amount of the composition of claim 1 to the patient.

12. The method of claim 11, wherein the composition further comprises CD44 which specifically targets the at least one membrane for endothelial glycocalyx restoration.

13. A method of treating cardiovascular disease (CVD) in a patient in need thereof, comprising administering an effective amount of the composition of claim 1 to an individual suffering from CVD, wherein the composition is targeted to endothelial membranes.

14. The method of claim 13, wherein the administration of the effective amount of the composition of claim 1 restores the glycocalyx, reverses inflammation, and reverses oxidative damage in the endothelial membranes.

15. The method of claim 13, wherein the administration is by injection.

16. The method of claim 13, wherein the administration is nasal, sublingual, percutaneous, or intestinal.

* * * * *